(12) United States Patent
Nicol et al.

(10) Patent No.: US 11,643,449 B2
(45) Date of Patent: May 9, 2023

(54) CALCIUM-CHELATING PEPTIDES DERIVED FROM EF-HAND CALCIUM-BINDING MOTIF

(71) Applicants: SORBONNE UNIVERSITÉ, Paris (FR); CENTRE NATIONAL DE LA RECHERCHE SCIENTIFIQUE, Paris (FR); INSTITUT NATIONAL DE LA SANTE ET DE LA RECHERCHE MEDICALE (INSERM), Paris (FR)

(72) Inventors: Xavier Nicol, Chatou (FR); Oriol Ros Torres, Paris (FR)

(73) Assignee: INSTITUT NATIONAL DE LA SANTÉ ET DE LA RECHERCHE MÉDICALE (INSERM), Paris (FR)

(*) Notice: Subject to any disclaimer, the term of this patent is extended or adjusted under 35 U.S.C. 154(b) by 193 days.

(21) Appl. No.: 16/759,975

(22) PCT Filed: Nov. 2, 2018

(86) PCT No.: PCT/EP2018/080032
§ 371 (c)(1),
(2) Date: Apr. 28, 2020

(87) PCT Pub. No.: WO2019/086617
PCT Pub. Date: May 9, 2019

(65) Prior Publication Data
US 2021/0179682 A1 Jun. 17, 2021

(30) Foreign Application Priority Data
Nov. 2, 2017 (EP) .................................... 17306514

(51) Int. Cl.
*C07K 14/47* (2006.01)
*A61K 38/00* (2006.01)

(52) U.S. Cl.
CPC .......... *C07K 14/4728* (2013.01); *A61K 38/00* (2013.01); *C07K 2319/02* (2013.01); *C07K 2319/60* (2013.01)

(58) Field of Classification Search
None
See application file for complete search history.

(56) References Cited

PUBLICATIONS

Shakya, S. "Characterization of Interaction of Calmodulin and its Chimeras with Orail", Thesis, Southern Illinois University Edwardsville, Aug. 2013.*
Hoeflich and Ikura, "Calmodulin in Action: Diversity in Target Recognition and Activation Mechanisms", Cell vol. 108, pp. 739-742, Mar. 22, 2002.*
The International Bureau of WIPO, International Report on Patentability issued in International Application No. PCT/EP2018/080032, dated May 5, 2020, 7 pages.
Durussel, I., et al., "Chimeras of Parvalbumin and Oncomodulin Involving Exchange of the Complete CD Site Show That the CA2+/MG2+ Specificity is an Intrinsic Property of the Site," European Journal of Biochemistry 242(2):256-263, Dec. 1996.
George, S., et al., "Chimeras of Calmodulin, Troponin C and Parvalbumin: Probes of Structure-Function Relationships in Smooth Muscle Contraction," Journal of Cellular Biochemistry, Supplement 15 Part C(15 Part C): 113, Jan. 1991.
George, S., et al., "Calmodulin-Cardiac Troponin C Chimeras: Effects of Domain Exchange on Calcium Binding and Enzyme Activation," Journal of Biological Chemistry 268(33): 25213-25220, 1993.
International Search Report dated Jan. 17, 2019, issued in corresponding International Application No. PCT/EP2018/080032, filed Nov. 2, 2018, 4 pages.
Lakowski, T.M., et al., "Calcium-Induced Folding of a Fragment of Calmodulin Composed of EF-Hands 2 and 3," Protein Science 16(6):1119-1132, Jun. 2007.
Written Opinion dated Jan. 17, 2019, issued in corresponding International Application No. PCT/EP2018/080032, filed Nov. 2, 2018, 6 pages.

* cited by examiner

*Primary Examiner* — Anand U Desai
(74) *Attorney, Agent, or Firm* — Christensen O'Connor Johnson Kindness PLLC

(57) ABSTRACT

The disclosure pertains to the field of molecular means capable of binding calcium, in particular peptides which are calcium chelators, appropriate for use in vitro or in vivo and preferably capable of targeting specific cellular compartments. Polypeptide comprising a first calcium-binding domain, a peptide linker and a second calcium binding domain, wherein the first and second binding domains are linked through the peptide linker, and wherein: the first calcium-binding domain and the second calcium binding domain each comprise at least one calcium-binding site derived from a EF-hand motif; and, the first calcium-binding domain and the second calcium binding domain differ in at least one calcium-binding site.

19 Claims, 11 Drawing Sheets
Specification includes a Sequence Listing.

SEQUENCE LISTING

```
<160> NUMBER OF SEQ ID NOS: 24

<210> SEQ ID NO 1
<211> LENGTH: 12
<212> TYPE: PRT
<213> ORGANISM: artificial
<220> FEATURE:
<223> OTHER INFORMATION: consensus sequence
<220> FEATURE:
<221> NAME/KEY: MISC_FEATURE
<222> LOCATION: (2)..(2)
<223> OTHER INFORMATION: Xaa is any amino-acid residue except W
<220> FEATURE:
<221> NAME/KEY: MISC_FEATURE
<222> LOCATION: (3)..(3)
<223> OTHER INFORMATION: Xaa is D, N or S
<220> FEATURE:
<221> NAME/KEY: MISC_FEATURE
<222> LOCATION: (4)..(4)
<223> OTHER INFORMATION: Xaa is any amino-acid residue, except I, L, V,
      F, Y and W
<220> FEATURE:
<221> NAME/KEY: MISC_FEATURE
<222> LOCATION: (5)..(5)
<223> OTHER INFORMATION: Xaa is D, E, N, S, T or G
<220> FEATURE:
<221> NAME/KEY: MISC_FEATURE
<222> LOCATION: (6)..(6)
<223> OTHER INFORMATION: Xaa is D, N, Q, G, H, R, or K
<220> FEATURE:
<221> NAME/KEY: MISC_FEATURE
<222> LOCATION: (7)..(7)
<223> OTHER INFORMATION: Xaa is any amino-acid residue except G and P
<220> FEATURE:
<221> NAME/KEY: MISC_FEATURE
<222> LOCATION: (8)..(8)
<223> OTHER INFORMATION: Xaa is L, I, V, M, or C
<220> FEATURE:
<221> NAME/KEY: MISC_FEATURE
<222> LOCATION: (9)..(9)
<223> OTHER INFORMATION: Xaa is D, E, N, Q, S, T, A, G or C
<220> FEATURE:
<221> NAME/KEY: MISC_FEATURE
<222> LOCATION: (10)..(10)
<223> OTHER INFORMATION: Xaa is any amino-acid residue
<220> FEATURE:
<221> NAME/KEY: MISC_FEATURE
<222> LOCATION: (11)..(11)
<223> OTHER INFORMATION: Xaa is any amino-acid residue
<220> FEATURE:
<221> NAME/KEY: MISC_FEATURE
<222> LOCATION: (12)..(12)
<223> OTHER INFORMATION: Xaa is E or D

<400> SEQUENCE: 1

Asp Xaa Xaa Xaa Xaa Xaa Xaa Xaa Xaa Xaa Xaa Xaa
1               5                   10

<210> SEQ ID NO 2
<211> LENGTH: 12
<212> TYPE: PRT
<213> ORGANISM: Rattus norvegicus
```

```
<400> SEQUENCE: 2

Asp Lys Asp Lys Ser Gly Phe Ile Glu Glu Asp Glu
1               5                   10

<210> SEQ ID NO 3
<211> LENGTH: 12
<212> TYPE: PRT
<213> ORGANISM: Homo sapiens

<400> SEQUENCE: 3

Asp Lys Asp Gly Asp Gly Lys Ile Gly Val Asp Glu
1               5                   10

<210> SEQ ID NO 4
<211> LENGTH: 12
<212> TYPE: PRT
<213> ORGANISM: Rattus norvegicus

<400> SEQUENCE: 4

Asp Lys Asp Gly Asp Gly Lys Ile Gly Val Glu Glu
1               5                   10

<210> SEQ ID NO 5
<211> LENGTH: 12
<212> TYPE: PRT
<213> ORGANISM: artificial
<220> FEATURE:
<223> OTHER INFORMATION: EF hand 1 of rat alpha parvalbulin- modified

<400> SEQUENCE: 5

Asp Lys Asp Lys Asp Gly Phe Ile Asp Glu Asp Glu
1               5                   10

<210> SEQ ID NO 6
<211> LENGTH: 12
<212> TYPE: PRT
<213> ORGANISM: Mus musculus

<400> SEQUENCE: 6

Asp Lys Asp Gly Asp Gly Thr Ile Thr Thr Lys Glu
1               5                   10

<210> SEQ ID NO 7
<211> LENGTH: 12
<212> TYPE: PRT
<213> ORGANISM: Mus musculus

<400> SEQUENCE: 7

Asp Ala Asp Gly Asn Gly Thr Ile Asp Phe Pro Glu
1               5                   10

<210> SEQ ID NO 8
<211> LENGTH: 12
<212> TYPE: PRT
<213> ORGANISM: Homo sapiens

<400> SEQUENCE: 8

Asp Lys Asp Gly Asn Gly Tyr Ile Ser Ala Ala Glu
1               5                   10

<210> SEQ ID NO 9
<211> LENGTH: 12
<212> TYPE: PRT
<213> ORGANISM: Homo sapiens
```

<400> SEQUENCE: 9

Asp Ile Asp Gly Asp Gly Gln Val Asn Tyr Glu Glu
1               5                   10

<210> SEQ ID NO 10
<211> LENGTH: 36
<212> TYPE: PRT
<213> ORGANISM: artificial
<220> FEATURE:
<223> OTHER INFORMATION: full EF hand 1 of rat alpha parvalbulin
      modified

<400> SEQUENCE: 10

Lys Ser Ala Asp Asp Val Lys Lys Val Phe His Ile Leu Asp Lys Asp
1               5                   10                  15

Lys Asp Gly Phe Ile Asp Glu Asp Glu Leu Gly Ser Ile Leu Lys Gly
            20                  25                  30

Phe Ser Ser Asp
        35

<210> SEQ ID NO 11
<211> LENGTH: 33
<212> TYPE: PRT
<213> ORGANISM: Rattus norvegicus

<400> SEQUENCE: 11

Leu Ser Ala Lys Glu Thr Lys Thr Leu Met Ala Ala Gly Asp Lys Asp
1               5                   10                  15

Gly Asp Gly Lys Ile Gly Val Glu Glu Phe Ser Thr Leu Val Ala Glu
            20                  25                  30

Ser

<210> SEQ ID NO 12
<211> LENGTH: 36
<212> TYPE: PRT
<213> ORGANISM: Mus musculus

<400> SEQUENCE: 12

Glu Gln Ile Ala Glu Phe Lys Glu Ala Phe Ser Leu Phe Asp Lys Asp
1               5                   10                  15

Gly Asp Gly Thr Ile Thr Thr Lys Glu Leu Gly Thr Val Met Arg Ser
            20                  25                  30

Leu Gly Gln Asn
        35

<210> SEQ ID NO 13
<211> LENGTH: 36
<212> TYPE: PRT
<213> ORGANISM: Mus musculus

<400> SEQUENCE: 13

Pro Thr Glu Ala Glu Leu Gln Asp Met Ile Asn Glu Val Asp Ala Asp
1               5                   10                  15

Gly Asn Gly Thr Ile Asp Phe Pro Glu Phe Leu Thr Met Met Ala Arg
            20                  25                  30

Lys Met Lys Asp
        35

<210> SEQ ID NO 14
<211> LENGTH: 36
<212> TYPE: PRT

<213> ORGANISM: Mus musculus

<400> SEQUENCE: 14

Asp Ser Glu Glu Ile Arg Glu Ala Phe Arg Val Phe Asp Lys Asp
1               5                   10                  15

Gly Asn Gly Tyr Ile Ser Ala Ala Glu Leu Arg His Val Met Thr Asn
                20                  25                  30

Leu Gly Glu Lys
            35

<210> SEQ ID NO 15
<211> LENGTH: 33
<212> TYPE: PRT
<213> ORGANISM: Mus musculus

<400> SEQUENCE: 15

Leu Thr Asp Glu Glu Val Asp Glu Met Ile Arg Glu Ala Asp Ile Asp
1               5                   10                  15

Gly Asp Gly Gln Val Asn Tyr Glu Glu Phe Val Gln Met Met Thr Ala
                20                  25                  30

Lys

<210> SEQ ID NO 16
<211> LENGTH: 110
<212> TYPE: PRT
<213> ORGANISM: artificial
<220> FEATURE:
<223> OTHER INFORMATION: EF hand 1 and 2 of rat alpha parvalbulin
      modified

<400> SEQUENCE: 16

Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
                20                  25                  30

Met Val Gly Leu Lys Lys Lys Ser Ala Asp Asp Val Lys Lys Val Phe
            35                  40                  45

His Ile Leu Asp Lys Asp Lys Asp Gly Phe Ile Asp Glu Asp Glu Leu
        50                  55                  60

Gly Ser Ile Leu Lys Gly Phe Ser Ser Asp Ala Arg Asp Leu Ser Ala
65                  70                  75                  80

Lys Glu Thr Lys Thr Leu Met Ala Ala Gly Asp Lys Asp Gly Asp Gly
                85                  90                  95

Lys Ile Gly Val Glu Glu Phe Ser Thr Leu Val Ala Glu Ser
            100                 105                 110

<210> SEQ ID NO 17
<211> LENGTH: 73
<212> TYPE: PRT
<213> ORGANISM: Mus musculus

<400> SEQUENCE: 17

Glu Gln Ile Ala Glu Phe Lys Glu Ala Phe Ser Leu Phe Asp Lys Asp
1               5                   10                  15

Gly Asp Gly Thr Ile Thr Thr Lys Glu Leu Gly Thr Val Met Arg Ser
                20                  25                  30

Leu Gly Gln Asn Pro Thr Glu Ala Glu Leu Gln Asp Met Ile Asn Glu
            35                  40                  45

Val Asp Ala Asp Gly Asn Gly Thr Ile Asp Phe Pro Glu Phe Leu Thr

Met Met Ala Arg Lys Met Lys Asp Thr
65              70

<210> SEQ ID NO 18
<211> LENGTH: 11
<212> TYPE: PRT
<213> ORGANISM: artificial
<220> FEATURE:
<223> OTHER INFORMATION: peptid linker

<400> SEQUENCE: 18

Ile Asp Leu Lys Met Ala Asp Gln Leu Thr Glu
1               5                   10

<210> SEQ ID NO 19
<211> LENGTH: 194
<212> TYPE: PRT
<213> ORGANISM: artificial
<220> FEATURE:
<223> OTHER INFORMATION: full length polypeptide

<400> SEQUENCE: 19

Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
            20                  25                  30

Met Val Gly Leu Lys Lys Lys Ser Ala Asp Asp Val Lys Lys Val Phe
        35                  40                  45

His Ile Leu Asp Lys Asp Lys Asp Gly Phe Ile Asp Glu Asp Glu Leu
    50                  55                  60

Gly Ser Ile Leu Lys Gly Phe Ser Ser Asp Ala Arg Asp Leu Ser Ala
65                  70                  75                  80

Lys Glu Thr Lys Thr Leu Met Ala Ala Gly Asp Lys Asp Gly Asp Gly
                85                  90                  95

Lys Ile Gly Val Glu Glu Phe Ser Thr Leu Val Ala Glu Ser Ile Asp
            100                 105                 110

Leu Lys Met Ala Asp Gln Leu Thr Glu Glu Gln Ile Ala Glu Phe Lys
        115                 120                 125

Glu Ala Phe Ser Leu Phe Asp Lys Asp Gly Asp Gly Thr Ile Thr Thr
    130                 135                 140

Lys Glu Leu Gly Thr Val Met Arg Ser Leu Gly Gln Asn Pro Thr Glu
145                 150                 155                 160

Ala Glu Leu Gln Asp Met Ile Asn Glu Val Asp Ala Asp Gly Asn Gly
                165                 170                 175

Thr Ile Asp Phe Pro Glu Phe Leu Thr Met Met Ala Arg Lys Met Lys
            180                 185                 190

Asp Thr

<210> SEQ ID NO 20
<211> LENGTH: 22
<212> TYPE: PRT
<213> ORGANISM: artificial
<220> FEATURE:
<223> OTHER INFORMATION: tandem of Lyn Kinase  N-terminus domain

<400> SEQUENCE: 20

Met Gly Cys Ile Lys Ser Lys Arg Lys Asp Lys Met Gly Cys Ile Lys
1               5                   10                  15

Ser Lys Arg Lys Asp Lys
            20

<210> SEQ ID NO 21
<211> LENGTH: 14
<212> TYPE: PRT
<213> ORGANISM: artificial
<220> FEATURE:
<223> OTHER INFORMATION: CaaX-polylysine motif of Kras

<400> SEQUENCE: 21

Lys Lys Lys Lys Lys Lys Ser Lys Thr Lys Cys Val Ile Met
1               5                   10

<210> SEQ ID NO 22
<211> LENGTH: 636
<212> TYPE: DNA
<213> ORGANISM: artificial
<220> FEATURE:
<223> OTHER INFORMATION: polynucleotide example 1

<400> SEQUENCE: 22
atgtcgatga cagacttgct cagcgctgag gacatcaaga aggcgatagg agcctttact      60
gctgcagact ccttcgacca caaaaagttc ttccagatgg tgggcctgaa gaaaaagagt     120
gcggatgatg tgaagaaggt gttccacatt ctggacaaag acaaagatgg cttcattgac     180
gaggatgagc tggggtccat tctgaagggc ttctcctcag atgccagaga cttgtctgct     240
aaggaaacaa agacgctgat ggctgctgga gacaaggacg gggatggcaa gattggggtt     300
gaagagttct ccactctggt ggccgaaagc atcgatctta agatggctga tcagctgact     360
gaagagcaga ttgctgaatt taaggaggct ttctccctat tcgataaaga tggtgacggc     420
accatcacaa ccaaggaact ggggaccgtc atgcggtcac tgggtcagaa cccaacagaa     480
gccgagctgc aggatatgat caacgaagtg gatgctgatg gcaatggcac cattgacttc     540
ccagagttct tgactatgat ggctagaaaa atgaaagaca cacttaaggc ggatcccgcc     600
acctgtacat acccatacga tgttccagat tacgct                              636

<210> SEQ ID NO 23
<211> LENGTH: 66
<212> TYPE: DNA
<213> ORGANISM: artificial
<220> FEATURE:
<223> OTHER INFORMATION: nucleotide sequence encoding the Lyn Kinase
      N-terminus domain

<400> SEQUENCE: 23
atgggctgca tcaagagcaa gcgcaaggac aagatgggct gcatcaagag caagcgcaag      60
gacaag                                                                66

<210> SEQ ID NO 24
<211> LENGTH: 46
<212> TYPE: DNA
<213> ORGANISM: artificial
<220> FEATURE:
<223> OTHER INFORMATION: sequence encoding the CaaX-polylysine motif of
      Kras

<400> SEQUENCE: 24
caagaagaag aagaagaaga agagcaagac caagtgcgtg atcatg                    46

CALCIUM-CHELATING PEPTIDES DERIVED FROM EF-HAND CALCIUM-BINDING MOTIF

The invention pertains to the field of molecular means capable of binding calcium, in particular peptides which are calcium chelators, appropriate for use in vitro or in vivo and preferably capable of targeting specific cellular compartments.

Calcium ($Ca^{2+}$) is a second messenger central in multiple cellular responses ranging from metabolism and survival to vesicle release and motility. The blockade of $Ca^{2+}$ signals currently relies on pharmacological strategies to block $Ca^{2+}$ influx into the cell or chelate the extracellular or intracellular $Ca^{2+}$. Since $Ca^{2+}$ is crucial for many signaling pathways and for the function of a wide range of components of the extracellular matrix, those strategies lack cellular specificity and are plagued with a variety of side effects when applied to patients. Since their first appearance, the rise of optogenetics has provided a wide variety of tools to increase intracellular $Ca^{2+}$. This has been widely used to control electrical activity in excitable cells and provided a vast knowledge focused on neuronal interactions and even opened new promising fields in therapeutics. Nevertheless, this strategy relies on imposing additional $Ca^{2+}$ influx from the extracellular medium, with no possibility of manipulating endogenous $Ca^{2+}$ variations, reduce $Ca^{2+}$ concentration or to target $Ca^{2+}$ release from internal stores. In addition, the use of optogenetics is handicapped in vivo, when light stimulation are technically challenging (e.g. during early stages of development).

There is thus a need for improved means to manipulate calcium signaling, and in particular intracellular calcium concentration.

The helix-loop-helix calcium-binding motif (EF-hand motif) is the most prevalent $Ca^{2+}$ binding site in proteins. The canonical EF-hand motif is of about 29 amino acids in length and is structured by two alpha-helices bridged by a flexible calcium-binding loop composed of 12 highly conserved residues.

The inventors have set up polypeptides comprising calcium-binding domains derived from EF hand motifs. As a result, the polypeptides of the invention interact directly with calcium, rather than modifying the activity of calcium channels. They can therefore be utilized as chelators of intracellular $Ca^{2+}$.

Said polypeptides are formed of two calcium-binding domains having different binding affinity for $Ca^{2+}$, and which are linked through a peptide linker. The inventors have in particular found that by associating calcium-binding domains derived from different EF-hand motif, and therefore having distinct affinities for $Ca^{2+}$, the range of calcium-dependent cellular pathways susceptible to be affected is enlarged.

The polypeptides of the invention can be used in vitro and in vivo, for instance to prevent the activation of downstream effectors and calcium-dependent cellular processes. The polypeptides of the invention can easily be further functionalized using simple molecular tools, for instance by addition of fluorescent peptides or signal peptides, so as to target specific compartments within the cells, and can thus be employed in a wide variety of applications.

The invention pertains to a polypeptide comprising a first calcium-binding domain, a peptide linker and a second calcium binding domain, wherein said first and second binding domains are linked through said peptide linker, and wherein:

the first calcium-binding domain and the second calcium binding domain each comprise at least one calcium-binding site derived from a EF-hand motif; and, the first calcium-binding domain and the second calcium binding domain differ in at least one calcium-binding site.

The polypeptide of the invention is preferably an isolated, recombinant or synthetic polypeptide.

In the context of the invention, the terms 'differ in at least one calcium-binding site_ indicates that at least one of the calcium binding sites of one calcium-binding domain differs from any of the calcium binding sites of the other calcium-binding domain.

In the context of the invention, the terms 'calcium-binding site derived from a EF-hand motif_ refer to peptide which sequence derives from the sequence of said EF hand motif by substitution, deletion or addition of amino-acid residues, and which has retained the ability to bind calcium.

The ability to bind calcium can easily be measured using well known methods, for instance using fluorescence methods such as thoroughly detailed by Johnson and Tikunova (Methods in Molecular Biology; 173: 89-102, 2002).

Preferably, each of the calcium-binding sites according to the invention derives from a canonical EF-hand motif.

In the context of the invention, the terms 'canonical EF-hand motif_ should be construed as generally considered in the field, that is to say as a peptide sequence comprising about 29 amino-acid residues containing a first a-helix designated as E (residues 1-10), a calcium-binding loop (residues 10-21), and a second a-helix designated F (residues 19-29). This motif has been found in a large number of calcium-binding proteins.

Preferably, in the polypeptide of the invention, the calcium-binding sites are derived from canonical EF-hand motif from proteins chosen in the list consisting of Parvalbumin, Calmodulin, Calretinin, D28K, Calbindin, Recoverin, Hippocalcin, NCS-1, MELC, Cacineurin B, MRLC, Caltractin, TnC, Squidulin, Grancalcin, Sorcin, ALG2, Calpain, CaPK, Spectin, sCaBP, and BM-40. Advantageously, the calcium-binding sites are derived from canonical EF-hand motif from proteins chosen in the list consisting of Parvalbumin and Calmodulin.

It has been documented in the field that the calcium-binding function of the canonical EF-hand motif relies mostly on the 12 amino-acid calcium-binding loop. Preferably, each of the calcium-binding sites according to the invention comprises or consists of a calcium-binding loop of a canonical EF-hand motif.

Unless otherwise indicated, the terms 'calcium-binding loop of a canonical EF-hand motif_ or 'calcium binding loop_ refer the sequence of 12 amino-acid residues corresponding to the calcium-binding loop of a canonical EF-hand. Canonical EF-hands, their sequence and in particular the 12-amino-acid sequence corresponding to their respective calcium-binding loop are well documented. Preferably, the terms 'calcium-binding loop of a canonical EF-hand motif_ refer to a peptide sequence corresponding to the consensus sequence SEQ ID NO: 1:

$D-X_1-X_2-X_3-X_4-X_5-X_6-X_7-X_8-X_9-X_{10}-X_{11}$, in which:

$X_1$ is any amino-acid residue except W;
$X_2$ is D, N or S;
$X_3$ is any amino-acid residue, except I, L, V, F, Y and W;
$X_4$ is D, E, N, S, T or G;
$X_5$ is D, N, Q, G, H, R, or K;
$X_6$ is any amino-acid residue except G and P;
$X_7$ is L, I, V, M, or C;

$X_8$ is D, E, N, Q, S, T, A, G or C;
$X_9$ is any amino-acid residue;
$X_{10}$ is any amino-acid residue; and,
$X_{11}$ is E or D,
or a functional variant thereof.

Parvalbumin has been described in the field as containing two different EF hand motifs: Parv EF-hand1 and 2, and thus comprises the 2 corresponding calcium-binding loops:
the calcium-binding loop of rat Parv EF-hand1 has the sequence DKDKSGFIEEDE (SEQ ID NO: 2), and;
the calcium-binding loop of human Parv EF-hand2 has the sequence DKDGDGKIGVDE (SEQ ID NO: 3), while the calcium-binding loop of the rat Parv EF-hand2 has the sequence DKDGDGKIGVEE (SEQ ID NO: 4).

Of note, a high affinity variant of the calcium-binding loop of the rat Parv EF-hand1 having the sequence DKDKDGFIDEDE (SEQ ID NO: 5), has also been disclosed.

Calmodulin has been described in the field as containing four different EF hand motifs: CaM EF-hand1, 2, 3 and 4, and thus comprises the 4 corresponding calcium-binding loops:
the calcium-binding loop of CaM EF-hand1 has the sequence DKDGDGTITTKE (SEQ ID NO: 6) in both human and mouse;
the calcium-binding loop of CaM EF-hand2 has the sequence DADGNGTIDFPE (SEQ ID NO: 7) in both human and mouse;
the calcium-binding loop of CaM EF-hand3 has the sequence DKDGNGYISAAE (SEQ ID NO: 8) in both human and mouse, and;
the calcium-binding loop of CaM EF-hand4 has the sequence DIDGDGQVNYEE (SEQ ID NO: 9) in both human and mouse.

Yet preferably, in the polypeptide of the invention, each of the calcium-binding sites comprises or consists of a calcium-binding loop chosen in the list consisting of SEQ ID NO: 2 to 9, and functional variants thereof.

In order to increase the capacity of the polypeptide of the invention to bind calcium ions, the person skilled in the art may consider using calcium-binding sites derived from whole canonical EF-hand motifs, that is to say comprising the two a-helix as well as the calcium-binding loop typical of the canonical EF-hand motif.

Advantageously, in the polypeptide of the invention, each of the calcium-binding sites comprises or consists of a canonical EF-hand motif.

Parvalbumin has been described in the field as containing two different EF hand motifs: Parv EF-hand1 and 2:
Parv EF-hand1 has the sequence KSADDVKKVFHILDKDKDGFIDEDEL-GSILKGFSSD (SEQ ID NO: 10); and;
Parv EF-hand2 has the sequence LSAKETKTL-MAAGDKDGDGKIGVEEFSTLVAES (SEQ ID NO: 11).

Calmodulin has been described in the field as containing four different EF hand motifs: CaM EF-hand1, 2, 3 and 4:
CaM EF-hand1 has the sequence EQI-AEFKEAFSLFDKDGDGTITTKELGTVMRSLGQN (SEQ ID NO: 12);
CaM EF-hand2 has the sequence PTEAELQDMINEV-DADGNGTIDFPEFLTMMARKMKD (SEQ ID NO: 13);
CaM EF-hand3 has the sequence DSEEEIRE-AFRVFDKDGNGYISAAELRHVMTNLGEK (SEQ ID NO: 14), and;
CaM EF-hand4 has the sequence LTDEEVDEMIREAD-IDGDGQVNYEEFVQMMTAK (SEQ ID NO: 15).

Yet preferably, in the polypeptide of the invention, each of the calcium-binding sites comprises or consists of a canonical EF-hand motif chosen in the list consisting of SEQ ID NO: 10 to 15 and functional variants thereof.

Advantageously, the first calcium-binding domain and the second calcium binding domain each comprises at least two calcium-binding sites derived from a EF-hand motif. Preferably, the calcium-binding sites within a calcium-binding domain are derived from EF hand motifs from the same protein, preferably chosen in the list disclosed above.

In a preferred embodiment, in the polypeptide of the invention, the first calcium-binding domain comprises calcium-binding sites derived from EF-hand motifs from Parvalbumin, and the second calcium-binding domain comprises calcium-binding sites derived from EF-hand motifs from Calmodulin.

Preferably, in said embodiment, the first calcium-binding domain comprises two calcium-binding sites derived from EF-hand motifs from Parvalbumin, and the second calcium-binding domain comprises two calcium-binding sites derived from EF-hand motifs from Calmodulin.

More preferably, in said embodiment, the first calcium-binding domain comprises at least one, preferably at least two, calcium-binding site comprising or consisting of calcium-binding loop from Parvalbumin chosen in the list consisting of SEQ ID NO: 2 to 5 and functional variants therefrom, yet preferably in the list consisting of SEQ ID NO: 4, SEQ ID NO: 5 and functional variants therefrom, and the second calcium-binding domain comprises at least one, preferably at least two, calcium-binding site comprising or consisting of calcium-binding loop from Calmodulin chosen in the list consisting of SEQ ID NO: 6 to 9 and functional variants therefrom, yet preferably in the list consisting of SEQ ID NO: 6 or 7 and functional variants thereof.

Yet preferably, in said embodiment, the first calcium-binding domain comprises or consists of at least one, preferably at least two, calcium-binding site comprising or consisting of EF-hand motifs from Parvalbumin chosen in the list consisting of SEQ ID NO: 10 and 11, and the second calcium-binding domain comprises or consists of at least one, preferably at least two, calcium-binding site comprising or consisting of EF-hand motifs from Calmodulin chosen in the list consisting of SEQ ID NO: 12 to 15 and functional variants therefrom, preferably in the list consisting of SEQ ID NO: 12 or 13 and functional variants thereof.

In a yet preferred embodiment, the first calcium-binding domain has a sequence comprising or consisting of the sequence SEQ ID NO: 16 or a functional variant thereof, and the second calcium-binding domain has a sequence comprising or consisting of the sequence SEQ ID NO: 17 or a functional variant thereof.

In the context of the invention, the functional variants of a sequence of reference chosen from SEQ ID NO: 1 to SEQ ID NO: 17 encompass peptides which sequence derives from said sequence of reference by insertions, substitutions, and/or deletions of amino-acid residues at one or more positions of the sequence of reference, and which have retained the ability to allow the localization of a peptide bound thereto or comprising thereof to lipid rafts. Of particular interest are the functional variants which sequence contains conservative substitutions, that is to say wherein amino acids residues of the sequence of reference are substituted for other amino acid residues with similar chemical properties (e.g., charge or hydrophobicity) and therefore do not change the functional properties of the molecule).

Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Neutral hydrophilic amino acids, which can be substituted for one another, include asparagine, glutamine, serine and threonine. Preferably, a functional variant of a sequence of reference chosen from SEQ ID NO: 1 to SEQ ID NO: 17 is a peptide which sequence derives from the sequence of reference by one or more conservative substitutions. Yet preferably, a functional variant of a sequence of reference chosen from SEQ ID NO: 1 to SEQ ID NO: 17 has a sequence which has at least 80, 85, 90 or 95% identity with the sequence of reference. In a preferred embodiment, a functional variant of sequence of reference chosen from SEQ ID NO: 1 to SEQ ID NO: 17 has a sequence which has at least 80, 85, 90 or 95% identity with the sequence of reference and is a peptide which sequence derives from the sequence of reference by conservative substitutions.

In the sense of the present invention, the "percentage identity" or "% identity" between two sequences of nucleic acids or amino acids means the percentage of identical nucleotides or amino acid residues between the two sequences to be compared, obtained after optimal alignment, this percentage being purely statistical and the differences between the two sequences being distributed randomly along their length. The comparison of two nucleic acid or amino acid sequences is traditionally carried out by comparing the sequences after having optimally aligned them, said comparison being able to be conducted by segment or by using an "alignment window". Optimal alignment of the sequences for comparison can be carried out, in addition to comparison by hand, by means of the local homology algorithm of Smith and Waterman, by means of the similarity search method of Pearson and Lipman (1988) or by means of computer software using these algorithms (GAP, BESTFIT, FASTA and TFASTA in the Wisconsin Genetics Software Package, Genetics Computer Group, 575 Science Dr., Madison, Wis., or by the comparison software BLAST NR or BLAST P). The percentage identity between two nucleic acid or amino acid sequences is determined by comparing the two optimally-aligned sequences in which the nucleic acid or amino acid sequence to compare can have additions or deletions compared to the reference sequence for optimal alignment between the two sequences. Percentage identity is calculated by determining the number of positions at which the amino acid, nucleotide or residue is identical between the two sequences, preferably between the two complete sequences, dividing the number of identical positions by the total number of positions in the alignment window and multiplying the result by 100 to obtain the percentage identity between the two sequences.

The polypeptide of the invention further comprises a peptide linker

Preferably, the peptide linker according to the invention has a length of at least 5, preferably at least 10, and up to 40, preferably up to 30, and still more preferably up to 20 amino-acids. Preferably the peptide linker has the sequence SEQ ID NO: 18.

In a preferred embodiment, the polypeptide of the invention has the sequence SEQ ID NO: 19.

The polypeptide of the invention may further be functionalized with peptide sequences having properties of interest, such as peptide signals, which are localization sequences that will enable targeting the polypeptide of the invention to specific subcellular compartment, or fluorescent peptides, that will be useful for in vitro detection of the polypeptide.

Peptides signals capable of targeting a polypeptide to specific subcellular compartment are well known in the art. Of particular interest are the sequences capable of targeting peptides to the plasma membrane, and more particularly to lipid rafts. Lipid rafts are sphingolipid- and cholesterol-rich plasma membrane microdomains, which have been identified and proposed to function as platforms where signal transduction molecules may interact with receptors. Peptide signals capable of targeting a peptide to the plasma membrane are well known in the art. For instance, the N terminus domains of proteins from the Src family, and in particular the peptide of sequence SEQ ID NO: 20, which corresponds to the palmitoylation and myristoylation motifs of the N terminus part of the Lyn Kinase, have been shown to enable the localization of said proteins to lipid rafts. In contrast, the peptide of sequence SEQ ID NO: 21 which corresponds to the CaaX-polylysine motif derived from the protein K-Ras, is known to target proteins to the plasma membrane while excluding the localization to lipid rafts. Advantageously, the polypeptide of the invention further comprises a peptide signal, preferably a peptide signal capable of targeting the polypeptide of the invention to the plasma membrane, yet preferably to lipid rafts of the plasma membrane. Preferably, the polypeptide of the invention further comprises a peptide signal of sequence SEQ ID NO: 20 or 21, or functional variants thereof.

In the context of the invention, the functional variants of SEQ ID NO: 20 encompass peptides which sequence derives from the sequence SEQ ID NO: 20 by insertions, substitutions, and/or deletions of amino-acid residues at one or more positions of the sequence SEQ ID NO: 20, and which have retained the ability to allow the localization of a peptide bound thereto or comprising thereof to lipid rafts. Of particular interest are the functional variants which sequence contains conservative substitutions, that is to say wherein amino acids residues of the sequence SEQ ID NO: 20 are substituted for other amino acid residues with similar chemical properties (e.g., charge or hydrophobicity) and therefore do not change the functional properties of the molecule). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Neutral hydrophilic amino acids, which can be substituted for one another, include asparagine, glutamine, serine and threonine. Preferably, a functional variant of SEQ ID NO: 20 is a peptide which sequence derives from the sequence SEQ ID NO: 20 by one or more conservative substitutions. Yet preferably, a functional variant of SEQ ID NO: 20 has a sequence which has at least 80, 85, 90 or 95% identity with the sequence SEQ ID NO: 20. In a preferred embodiment, a functional variant of SEQ ID NO: 20 has a sequence which has at least 80, 85, 90 or 95% identity with the sequence SEQ ID NO: 20 and is a peptide which sequence derives from the sequence SEQ ID NO: 20 by conservative substitutions.

In the context of the invention, the functional variants of SEQ ID NO: 21 encompass peptides which sequence derives from the sequence SEQ ID NO: 21 by insertions, substitutions, and/or deletion, of amino-acid residues at one or more positions of the sequence of reference, and which have retained the ability to allow the localization of a peptide bound thereto or comprising thereof to the cellular membrane, at the exclusion of lipid rafts. Of particular interest are the functional variants which sequence contains conservative substitutions, that is to say wherein amino acids residues of the sequence SEQ ID NO: 21 are substituted for other amino acid residues with similar chemical properties (e.g., charge or hydrophobicity) and therefore do not change the functional properties of the molecule). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Neutral hydrophilic amino acids, which can be substituted for one another, include asparagine, glutamine, serine and threonine. Preferably, a functional variant of SEQ ID NO: 21 is a peptide which sequence derives from the sequence SEQ ID NO: 21 by one or more conservative substitutions. Yet preferably, a functional variant of SEQ ID NO: 21 has a sequence which has at least 80, 85, 90 or 95% identity with the sequence SEQ ID NO: 21. In a preferred embodiment, a functional variant of SEQ ID NO: 21 has a sequence which has at least 80, 85, 90 or 95% identity with the sequence SEQ ID NO: 21 and is a peptide which sequence derives from the sequence SEQ ID NO: 21 by conservative substitutions.

The capacity of a peptide signal to allow the localization of a peptide bound thereto or comprising thereof to the cellular membrane, and in particular to lipid rafts or at the exclusion of lipid rafts may easily be determined using standard methods, in particular based on fluorescence microscopy and/or density gradients, such as detailed in the experimental part of the present application The peptide signal may be in the C terminus or the N terminus part of the polypeptide.

Fluorescent peptides are well known in the art. Examples of fluorescent peptides are the green fluorescent protein (GFP), or GFP variants such as cyan fluorescent protein (CFP), yellow fluorescent protein (YFP) and red fluorescent protein (RFP) and their variants such as the optimized CFP Turquoise or the YFP variant Venus. Advantageously, the polypeptide of the invention further comprises a fluorescent peptide, preferably chosen in the list consisting of green fluorescent protein (GFP), cyan fluorescent protein (CFP), yellow fluorescent protein (YFP) and red fluorescent protein (RFP), and their variants such as the optimized CFP Turquoise or the YFP variant Venus. The fluorescent protein may be in the C terminus or the N terminus part of the polypeptide.

Preferably, the invention also pertains to modified polypeptides, which are derived from the polypeptide of the invention or its functional variants by introduction of chemical modification into one or more amino acid residues, peptide bonds, N- and/or C-terminal ends of the protein, aimed at increasing the stability, bioavailability or bioactivity of the protein, as long as the modified polypeptide remains functional.

Another aspect of the invention relates to a polynucleotide encoding the polypeptide of the invention, and a recombinant vector encoding said polynucleotide.

In the context of the invention, the term 'polynucleotide_ refers to a polydeoxyribonucleotides or polyribonucleotides, in the form of a separate fragment or a larger construct, and includes DNA, cDNA and RNA sequences which encode the polypeptide of the invention. Preferably, the polynucleotide of the invention is an isolated polynucleotide. The term 'isolated_ as used herein includes polynucleotides substantially free of other nucleic acids, proteins, lipids, carbohydrates or other materials with which it is naturally associated.

Preferably, said recombinant vector is an expression vector capable of expressing said polynucleotide when transfected or transformed into a host cell such as a eukaryotic or prokaryotic cell like a mammalian, bacterial or fungal cell. 'Expression vectors_ are DNA sequences that are required for the transcription of cloned DNA and the translation of their mRNAs in an appropriate host. An appropriately constructed expression vector may contain: an origin of replication for autonomous replication in host cells, selectable markers, a limited number of useful restriction enzyme sites, a potential for high copy number, and active promoters. Suitable selectable markers may for instance be chosen among the genes encoding neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine-guanine phosphoribosyl transferase for eukaryotic cell culture; TRP1 for *S. cerevisiae*. Some expression vectors do not contain an origin of replication for autonomous replication in host cells but rather depend on the ability of the vector to stably integrate (either randomly or by a homologous integration event) using a marker to select for integration/maintenance. A promoter is defined as a DNA sequence that directs RNA polymerase to bind to DNA and initiate RNA synthesis. A strong promoter is one which causes mRNAs to be initiated at high frequency. The polynucleotide is inserted into the expression vector in proper orientation and correct reading frame for expression. Preferably, the polynucleotide is operably linked to at least one transcriptional regulatory sequence and, optionally to at least one translational regulatory sequence. Such vectors comprise YAC (yeast artificial chromosome), BAC (bacterial artificial), baculovirus vectors, phage, phagemid, cosmid, viral vector, plasmid, RNA vector or a linear or circular DNA or RNA molecule which may consist of chromosomal, non chromosomal, semi-synthetic or synthetic DNA. Suitable vectors according to the present invention comprise, but are not limited to, YAC (yeast artificial chromosome), BAC (bacterial artificial), baculovirus vectors, phage, phagemid, cosmid, viral vector, plasmid, RNA vector or a linear or circular DNA or RNA molecule which may consist of chromosomal, non chromosomal, semi-synthetic or synthetic DNA. Suitable plasmids to be used as mammalian expression vectors include but are not limited to, pcDNA3, pcDNA3.1, pcDNAI, pcDNAIamp (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and ≅ZD35 (ATCC 37565). Suitable plasmids to be used as bacterial expression vectors include but are not limited to pCR2.1 (Invitrogen), pET11a (Novagen), lambda gt11 (Invitrogen), pcDNAII (Invitrogen), pKK223-3 (Pharmacia), and pQE vectors (Qiagen) including pQE7O, pQE6O, pQE-9. Suitable plasmids to be used as expression vectors in fungal cells include but are not limited to pYES2 (Invitrogen), *Pichia* expression vector (Invitrogen). Suitable plasmids to be used as expression vectors in insect cell include but are not limited to pBlueBacIII, pBlueBacHis2 (Invitrogen) and pFastBac1, pFastBacHT (Life Technologies). Viral vectors include retrovirus, adenovirus, parvovirus (e. g., adenoassociated viruses), coronavirus, negative strand RNA viruses such as ortho-myxovirus (e. g., influenza virus), rhabdovirus (e. g., rabies and vesicular stomatitis virus), paramyxovirus (e. g. measles and Sendai), positive strand RNA viruses such as picornavirus and alphavirus, and double stranded DNA viruses including adenovirus, herpesvirus (e. g., Herpes Simplex virus types 1 and 2, Epstein-Barr virus, cytomegalovirus), and poxvirus (e. g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, Dtype viruses, HTLV-BLV group, lentivirus, spumavirus. Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses.

Another aspect of the invention provides a host cell or a non-human organism transformed with said polynucleotide or recombinant vector. The non-human transgenic organism is obtained from a unicellular or pluricellular microorganism or a higher eukaryotic organism. The expression vector may be introduced into host cells via any one of a number of techniques including but not limited to infection, transformation, transfection, lipofection, protoplast fusion, and electroporation. Modified host cells containing the expression vector may be clonally propagated and individually analyzed to determine whether they produce the polypeptide of the invention.

In a preferred embodiment said modified host cell is a eukaryotic cell such as a human cell. In another embodiment, said non-human transgenic organism is a transgenic plant, nematode, zebrafish or algae.

The polynucleotide, vector, host cell, and non-human transgenic organism of the invention are useful for the production of the polypeptide/chimeric protein of the invention using well-known recombinant DNA techniques. Another aspect of the invention relates to the non-therapeutic use of the polypeptide, polynucleotide, or vector comprising thereof, in vitro or in vivo, as calcium chelating agent. Preferably the invention relates to the non-therapeutic use of the polypeptide, polynucleotide, or vector comprising thereof for stabilizing and/or lowering calcium concentration, and/or for inhibiting calcium signalization in vivo and/or in vitro. Yet preferably, the non-therapeutic use, when performed in vivo, is performed in a healthy subject.

The terms 'stabilizing calcium concentration_ should be construed as generally understood in the art, that is to say as the action of minimizing the variations of the concentration of calcium in a composition upon addition of calcium or induction of calcium concentration variations in said composition. The variation, and in particular the increase, of calcium concentration may easily be measured using for instance the biosensor Twitch2B, by monitoring the FRET/CFP ratio, as disclosed in the experimental part. In the context of the invention, calcium concentration can be considered as stabilized in a composition when the FRET/CFP ratio of the biosensor Twitch2B varies, preferably increases, of less than 10%, preferably less than 5%, of the variation detected without the polypeptide of the invention upon of addition of calcium or induction of calcium concentration variations in said composition.

The terms 'inhibiting calcium signal_, 'calcium signal inhibition_ should be construed as generally understood in the art, that is to say as the action of inhibiting the downstream effectors known to be activated by calcium as a second messenger, for instance calcineurin. Methods and kits for assessing the calcineurin cellular activity are known and in the art, such as for instance the calcineurin cellular activity assay kit commercialized by the company Enzo (under reference BML-AK816-0001).

It is well documented that a number of pathologies are associated with calcium signaling dysfunction. The polypeptide, polynucleotide, vector, and host cell of the invention, may thus be particularly useful in preventing or treating such pathologies. In this context, the polypeptide, polynucleotide, vector, or host cell of the invention, may be formulated into a composition suitable for pharmaceutical use.

Another aspect of the invention relates to a pharmaceutical composition, comprising at least one polypeptide, polynucleotide, vector, and/or host cell of the invention, and, preferably, a pharmaceutically acceptable carrier. In the context of the invention, the terms "pharmaceutically acceptable" refer to carriers which can be used in the preparation of a pharmaceutical composition which is generally safe, non-toxic and neither biologically nor otherwise undesirable, and which is acceptable for veterinary use as well as for human pharmaceutical use. Suitable vehicles or carriers include any pharmaceutically acceptable vehicle such as buffering agents, stabilizing agents, diluents, salts, preservatives, and emulsifying agents. Examples of suitable buffering agents include buffered solutes, such as phosphate buffered solution, chloride solutions or Ringer˜s solution. Examples of suitable stabilizing agents include human serum albumin (HSA), polyvinylpyrrolidone or hyaluronic acid.

The composition of the invention may be formulated according to the intended administration route. For instance, formulations suitable for oral administration include liquid or solid formulations such as tablets, pills, powders (hard or soft gelatine capsules) or granules. Typically, in such formulations, the polypeptide, polynucleotide, vector, and/or host cell of the invention is mixed with one or more inert diluents such as starch, cellulose, sucrose, lactose or silica, in a stream of argon. These compositions may also comprise substances other than diluents, for example lubricants such as magnesium stearate or talc, coloring agent, coating (coated tablets) or varnish. Formulations suitable for injection, such as used in parenteral administration, are preferably sterile and fluid, and may preferably be aqueous or non-aqueous solutions, suspensions or emulsions.

Another aspect of the invention relates to the polypeptide, the polynucleotide, vector comprising thereof, host cell of the invention, or a composition comprising thereof for use as a medicine, preferably for use in the prevention and/or treatment of pathologies associated with intracellular calcium signaling dysfunction.

In the context of the invention, the terms 'pathologies associated with intracellular calcium signaling dysfunction_ should be construed according to their general meaning in the art. Preferably, said pathologies are associated with intracellular calcium signaling dysfunction due to an abnormally high intracellular concentration of calcium. In the context of the invention, 'an abnormally high intracellular concentration of calcium_ refer to an intracellular concentration of calcium which is significantly higher than in cells from a healthy donor. Yet preferably, said pathologies are chosen in the list consisting of retinitis pigmentosa, neurodegenerative diseases, preferably Alzheimer disease, epilepsy, stroke, cardiac dysrhythmia, heart failure, hypertension, diabetes, and cancer.

In other terms, the invention pertains to a method for the prevention and/or treatment of pathologies associated with intracellular calcium signaling dysfunction, wherein said pathologies are chosen in the list consisting of retinitis pigmentosa, neurodegenerative diseases, preferably Alzheimer disease, epilepsy, stroke, cardiac dysrhythmia, heart failure, hypertension, diabetes, and cancer, comprising the step of administering the polypeptide, polynucleotide, vector, host cell of the invention, or a composition comprising thereof to a subject in need thereof, preferably in an effective amount.

In the context of the invention, the terms 'effective amount_ means that the amount of polypeptide, polynucleotide, vector, host cell of the invention, or of a composition comprising thereof is of sufficient quantity to obtain appropriate prevention and or regression of the symptoms of the above-recited pathologies. The effective amount and dosage regimen may be determined by the attending physician based on usual clinical factors. As is well known in the medical arts, dosages for any one patient depends upon many factors, including the patient's size, body surface area, age, the particular compound to be administered, sex, time and route of administration, general health, and other drugs being administered concurrently.

The polypeptide, polynucleotide, vector, host cell of the invention, or composition comprising thereof referred to herein can administered once or more than one time, in order to prevent or to treat a pathology as recited herein. Efficacy of the prevention and/or treatment can be monitored by periodic assessment.

The polypeptide, polynucleotide, vector, host cell of the invention, or composition comprising thereof referred to herein can be administered topically or systemically, through the known routes of administration. Preferably, the polypeptide, polynucleotide, vector, host cell of the invention, or composition comprising thereof referred to herein is administered through the enteric route, in particular by oral, sublingual, or rectal administration, or through the parenteral route, in particular by intracerebral, intramuscular, intradermal, transdermal, intraperitoneal or nasal administration.

BRIEF DESCRIPTION OF THE DRAWINGS

In addition to the preceding features, the invention further comprises other features which will emerge from the following description, which refers to examples illustrating the present invention, as well as to the appended figures.

EXAMPLE 1

Figure 1:
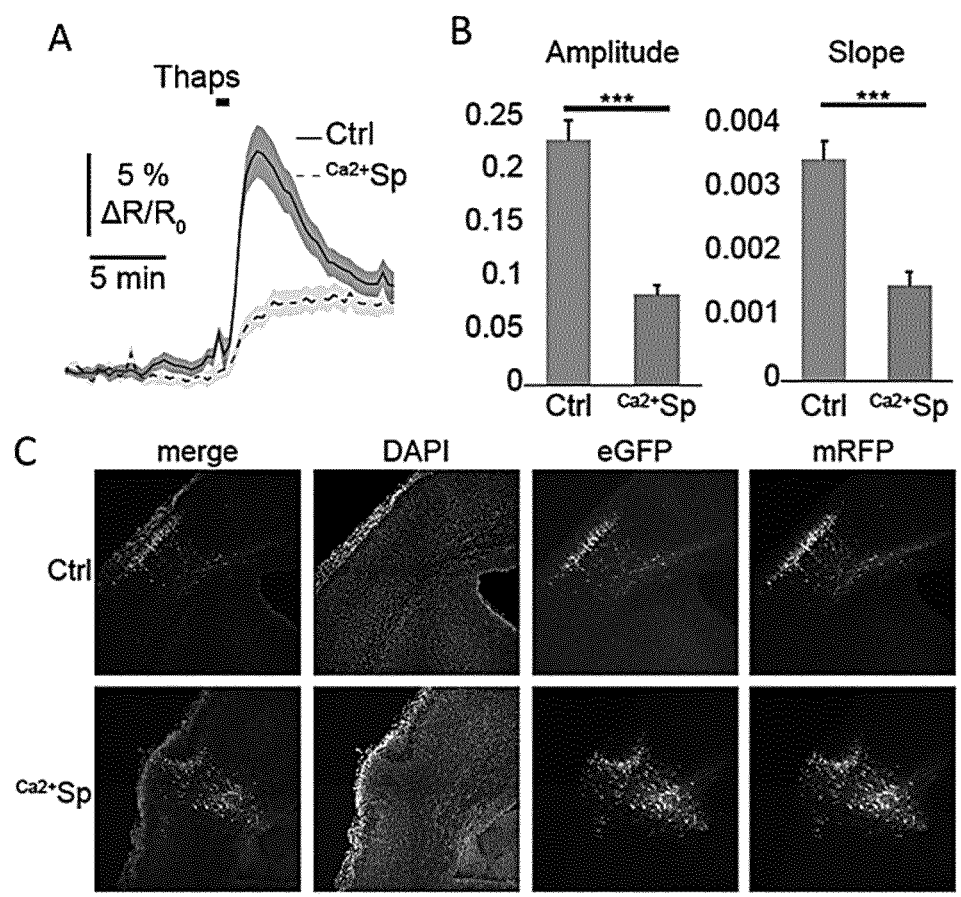
FIG. 1. The polypeptide of the invention is a $Ca^{2+}$ scavenger and alters cortical neuron migration in vivo. (A,B) 20 s thapsigargin (Thaps.) exposure induces an increase in the calcium concentration of control H293 cells, monitored by the FRET/CFP ratio from the FRET biosensor Twitch2B. In contrast, this elevation is drastically reduced when cells express $^{Ca2+}$Sp/SpiCee. FRET ratio is coded from blue (low $Ca^{2+}$) to red (high $Ca^{2+}$). (C) E14.5 eGFP and mRFP co-electroporated cortical neurons are packed into a dense layer close to the marginal zone at E18.5 (top row). In contrast $^{Ca2+}$Sp/SpiCee-expression prevents the development of this layer, with neurons scattered throughout the depth of the developing cortex, and the formation of heterotopia at the surface of the cortex (bottom row).

Constructs:

The polynucleotide of sequence SEQ ID NO:22 5ˇATGT-CGATGACAGACTTGCTCAGCGCTGAGGACATCAA-GAAGGCGATAG GAGCCTTTACTGCTGCAGACTCC-TTCGACCACAAAAAGTTCTTCCAGATGG TGGGCC-TGAAGAAAAGAGTGCGGATGATGTGAAGAAGG-TGTTCCACATT CTGGACAAAGACAAAGATGGCTT-CATTGACGAGGATGAGCTGGGGTCCAT TCTGAAG-GGCTTCTCCTCAGATGCCAGAGACTTGTCTGCTA-AGGAAACAAA GACGCTGATGGCTGCTGGGAGAC-AAGGACGGGGATGGCAAGATTGGGGTTGAAGA GT-TCTCCACTCTGGTGGCCGAAAGCATCGATCTTAA-GATGGCTGATC AGCTGACTGAAGAGCAGATTGCT-GAATTTAAGGAGGCTTTCTCCCTATTCG ATAAAGA-TGGTGACGGCACCATCACAACCAAGGAACTGGG-GACCGTCATG CGGTCACTGGGTCAGAACCCAACA-GAAGCCGAGCTGCAGGATATGATCAA CGAAGTGG-ATGCTGATGGCAATGGCACCATTGACTTCCCAGA-GTTCTTGAC TATGATGGCTAGAAAAATGAAAGA-CACACTTAAGGCGGATCCCGCCACCT GTACATACC-CATACGATGTTCCAGATTACGCT-3ˇ encoding a polynucleotide according to the invention, was designed in silico in frame with a tandem repeat of the nucleotide sequence encoding the Lyn Kinase N-terminus domain of sequence SEQ ID NO: 23: 5ˇ ATGGGCTGCAT-CAAGAGCAAGCGCAAGGACAAGATGGGCTGCAT-CAAG AGCAAGCGCAAGGACAAG3ˇ:

and the desired sequences obtained as oligonucleotides from Sigma and Invitrogen, respectively. The oligos were annealed and cloned into pcDNA3-mRFP in frame with the reporter sequence. Lipid-raft-excluded and cytosolic forms were obtained by subcloning the above polynucleotide into pcDNA3 with or without the sequence encoding the CaaX-polylysine motif of Kras of sequence SEQ ID NO: 24: 5ˇ CAAGAAGAAGAAGAAGAAGAAGAGCAAGACCA AGTGCGTGATCATG3ˇ respectively.

For expression on retinal ganglion cell (RGCs), the constructs were subcloned into pcX. Twitch2B was targeted to the membrane microdomains using the In-Fusion HD cloning kit (Clontech) and subcloned into pcDNA3 or pcX.

Cell culture: HEK293T cells were kept in a 37° C., 5% CO2 incubator and transfected using Lipofectamine 2000 (Invitrogen) according to the manufacturerˇs protocol and imaged the day following transfection or fixed and processed for immunocytofluorescence.

Production of purified $^{Ca2+}$Sp/SpiCee$^{F134W}$ and $^{Ca2+}$Sp/SpiCee$^{F103W}$: The full-length CaSponge cDNA was subcloned into a pGST-Parallel2 vector (derived from pGEX-4T-1; Amersham) in frame with the N-terminal glutathione S-transferase (GST) tag. $^{Ca2+}$Sp/SpiCee$^{F134W}$ and $^{Ca2+}$Sp/SpiCee$^{F103W}$ clones were prepared from $^{Ca2+}$Sp/SpiCee using the QuickChange II Site-directed mutagenesis kit (Agilent Technologies). Proteins were produced in BL21 (DE3) pLysS E. coli cells. The GST-tagged proteins were purified using a glutathione Sepharose 4B column. The GST tag was cleaved using recombinant tobacco etch virus NIa proteinase. The recombinant proteins were eluted in a buffer containing 30 mM MOPS (3-Morpholinopropanesulfonic acid), pH 7.2 and 100 mM KCl. Protein concentrations were deduced from A280 measurements using a computed extinction coefficient of 5500 M$^{-1}$ cm$^{-1}$ for both $^{Ca2+}$Sp/SpiCee$^{F134W}$ and $^{Ca2+}$Sp/SpiCee$^{F103W}$.

Measurement of Ca$^{2+}$ affinity for the labeled site of $^{Ca2+}$Sp/SpiCee$^{F103W}$ (parvalbumin-derived): Ca$^{2+}$ binding to the labeled site of $^{Ca2+}$Sp/SpiCee$^{F103W}$ was monitored by measuring tryptophan fluorescence (285 nm excitation, 330 nm emission, 5 nm bandpass) at 20° C. in a 4 mm×10 mm quartz cuvette (Jasco FP-8300 spectrofluorimeter). The protein was diluted to 2.25 µM in standard buffer (30 mM MOPS-KOH pH7.2; 0.1 M KCl) and 254 µL samples were loaded in the cuvette. It was first observed that addition of CaCl$_2$ did not increase fluorescence, whereas addition of millimolar amounts of EGTA led to large decreases (up to 27% at a final EGTA concentration of 7.5 mM). This showed that the labeled site of $^{Ca2+}$Sp/SpiCee$^{F103W}$ was saturated with Ca$^{2+}$. Dissociation constant of Ca$^{2+}$ was deduced from a competition experiment in which the protein solution was titrated with EGTA. 2 µl samples of solutions containing increasing concentrations of EGTA (1.95 to 500 mM) were added to the cuvette. Fluorescence was measured after each addition. Fluorescence values were corrected for dilution and plotted as a function of the concentration of EGTA. Data were fitted to the quadratic equation 1 as described previously by Weeks, K. M. & Crothers (D. M. Biochemistry 31, 10281-10287 (1992)), assuming that the two parvalbumin-derived sites were equivalent for Ca$^{2+}$ binding.

Measurement of Ca$^{2+}$ affinity for the labeled site of $^{Ca2+}$Sp/SpiCee$^{F134W}$ (calmodulin-derived): Ca$^{2+}$ binding to the first calmodulin site of $^{Ca2+}$Sp/SpiCee$^{F134W}$ was monitored by measuring tryptophan fluorescence (285 nm excitation, 340 nm emission, 5 nm bandpass) at 20° C. $^{Ca2+}$Sp/SpiCee$^{F134W}$ was diluted to 1.6 µM in standard buffer and 258 µL samples were loaded in the cuvette. Addition of CaCl$_2$ increased fluorescence, whereas addition of millimolar amounts of EGTA led to fluorescence decrease, showing that the calmodulin-derived sites of $^{Ca2+}$Sp/SpiCee were partially filled with Ca$^{2+}$ in the sample. The value of the fluorescence of the protein with Ca$^{2+}$-free calmodulin sites was measured in the presence of 2 mM EGTA, a concentration found to be saturating. Total concentration of Ca$^{2+}$ in the sample (excluding Ca$^{2+}$ bound to the parvalbumin derived sites of $^{Ca2+}$Sp/SpiCee) was measured as described above using Quin-2 and found to be 2.5 µM. Dissociation constant of Ca$^{2+}$ from the labeled site of $^{Ca2+}$Sp/SpiCee$^{F134W}$ was deduced from an experiment where the protein solution was titrated with increasing amounts of CaCl$_2$ (2 µL additions of solutions from 0.05 to 6.25 mM). Fluorescence values were corrected for dilution, and plotted as a function of total Ca$^{2+}$ concentration (added Ca$^{2+}$ plus 2.5 µM). Data were fitted to a binding curve assuming that the two calmodulin sites were equivalent for Ca$^{2+}$ binding.

Measurement of kinetic dissociation constants: Values of kinetic dissociation constants ($k_{off}$) for the tryptophan-labeled Ca binding sites of $^{Ca2+}$/Sp/SpiCee ($^{Ca2+}$Sp/SpiCee$^{F103W}$ and $^{Ca2+}$Sp/SpiCee$^{F134W}$) were measured by mixing proteins with appropriate amounts of EGTA at 20° C. in an Applied Photophysics stopped flow apparatus. Reacting solutions were excited at 285 nm and fluorescence was measured using a photomultiplier equipped with a 320 nm cutoff filter. For the $^{Ca2+}$Sp/SpiCee$^{F103W}$, the protein (2.3 µM in standard buffer) was mixed 1:1 with 15 mM EGTA in the same buffer. For $^{Ca2+}$Sp/SpiCee$^{F134W}$, the protein (1.7 µM in standard buffer plus 50 µM CaCl$_2$) was mixed 1:1 with 4 mM EDTA in standard buffer plus 50 µM CaCl$_2$. Fluorescence was recorded as a function of time and data were fitted with single exponential curves from which rate constants were derived. Reported values are the mean±standard deviation from three measurements.

Cell death assay: HEK293 Cells were plated on poly-lysine-coated coverslips and transfected the following day with a pCX-mRFP or a pCX-$^{Ca2+}$Sp/SpiCee vector using Lipofectamine 2000 (Thermo Fisher) following the manufacturer's instructions. Three days after plating, cells were either fixed with 4% paraformaldehyde and processed for immunocytochemistry with the antibodies against Cleaved Caspase 3 (Asp175; Cell Signaling; lot #0043) and -tubulin (Sigma) or treated with the CellEvent Caspase 3/7 Green Detection Reagent (Thermo Fisher) for 30 minutes and then fixed and labeled with an-tubulin antibody.

Membrane fractionation by detergent-free method: Electroporated retinas were pelleted (195 g for 5 min at 4° C.) and resuspended in 1.34 mL of 0.5 M sodium carbonate, pH 11.5, with protease inhibitor cocktail and phosphatase inhibitor cocktail 1, 2 and 3 (Sigma-Aldrich). The homogenate was sheared through a 26-gauge needle and sonicated three times for 20 s bursts. The homogenate was adjusted to 40% sucrose by adding 2.06 mL of 60% sucrose in MBS (25 mM MES, pH 6.4, 150 mM NaCl, and 250 mM sodium carbonate), placed under a 5-30% discontinuous sucrose gradient, and centrifuged at 34,000 rpm for 15-18 h at 4° C. in a Beckman SW 41Ti rotor. Nine fractions (1.24 mL each) were harvested from the top of the tube mixed with 9 volumes of MBS, and centrifuged at 40,000 rpm for 1 h at 4° C. (Beckman SW-41Ti rotor). Supernatants were discarded, and membrane pellets were resuspended in 100 µl of 1% SDS.

For immunoblotting, samples were separated on 4-15% Mini-Protean TGX Tris-Glycine-buffer SDS PAGE (Biorad) and transferred onto 0.2 µm Trans-Blot Turbo nitrocellulose membranes (Biorad). Membranes were blocked for one hour at room temperature in 1×TBS (10 mM Tris pH 8.0, 150 mM NaCl) supplemented with 5% (w/v) dried skim milk powder. Primary antibody incubation was carried out overnight at 4° C., with the following antibodies: rabbit anti-GFP (1/200; A11122; Life Technologies), rabbit anti-DsRed (1/200; 632476; Clontech), rabbit anti-ƒ-Adaptin (1/200; sc-10762; Santa Cruz) and rabbit anti-Caveolin (1/500; 610060; BD Transduction Laboratories). A goat anti-rabbit-HRP coupled secondary antibody was used for detection (Jackson ImmunoResearch, West Grove, Pa.). After antibody incubations, membranes were extensively washed in TBS T (TBS containing 2.5% Tween-20). Western blots were visualized using the enhanced chemiluminescence method (ECL prime Western Blotting detection reagent, Amersham).

Collapse assay: Retinas of E15 mice were electroporated with mRFP, Lyn-Calcium Sponge, Calcium Sponge or Calcium Sponge-Kras using two poring pulses (square wave, 175V, 5 ms duration, with 50 ms interval) followed by four transfer pulses (40V, 50 ms and 950 ms interpulse). Retinas were dissected and kept 24 hours in culture medium (DMEM-F12 supplemented with glutamine (Sigma Aldrich), penicillin/streptomicin (Sigma Aldrich), BSA (Sigma Aldrich) and glucose), in a humidified incubator at 37° C. and 5% CO2. The day after, they were cut into 200 µm squares with a Tissue-Chopper (McIlwan) and explants were plated on glass coverslips coated with poly-L-lysine and Laminin (Sigma Aldrich). Cells were cultured for 24 hours in culture medium supplemented with 0.4% methyl cellulose and treated with rmSlit-1 (R&D Systems) for 1 hour.

Immunodetection: Retinal explants, or Hek cells coexpressing the targeted versions of Calcium Sponge and GFP or the targeted versions of Twitch2B and mRFP, were fixed with 4% PFA in PB for 30 minutes, permeabilyzed blocked and with 1% Triton and 3% BSA in PBS, then immunized against DsRed (Clontech) followed by a secondary antibody coupled to AlexaFluor 594 (Invitrogen) and GFP (invitrogen) or -Tubulin (Sigma) followed by a secondary antibody coupled to AlexaFluor 488 (Invitrogen).

Imaging: Images were acquired with an inverted DMI6000B epifluorescence microscope (Leica) coupled to a 40× oil-immersion objective (N.A. 1.3) and the software Metamorph (Molecular Devices). For live imaging experiments, cells were perfused with HBS buffer with 0.2 or 2 mM CaCl. Thapsigargin was used at 1 mM). Images were acquired simultaneously for the CFP (483/32 nm) and YFP (542/27) channels every 20 seconds. Images were processed in ImageJ, corrected for background and bleedthrough and then the ratio CFP/YFP was calculated. Confocal images were acquired with a 63× oil immersion objective (N.A. 1.45) and a Z-stack containing the whole specimen was sampled at nyquist frequency. Images were rendered in ImageJ and Photoshop.

Statistics: Two-Way ANOVA and Bonferroni post-hoc tests were calculated with GraphPad Prism (GraphPad Software Inc.). **=p<0.001

Results:

An example of a polypeptide according to the invention, hereafter designated $^{Ca2+}$Sp, Calcium Sponge, SpiCee, or $^{Ca2+}$Sp/SpiCee those three terms referring to the exact same peptide, was designed as a fusion protein containing the Ca$^{2+}$ binding domains of both Parvalbumin and Calmodulin.

The fluorescent protein mRFP was fused to this construct for easy identification of sponge-expressing cells in fixed or live cell experiments.

Figure 5:
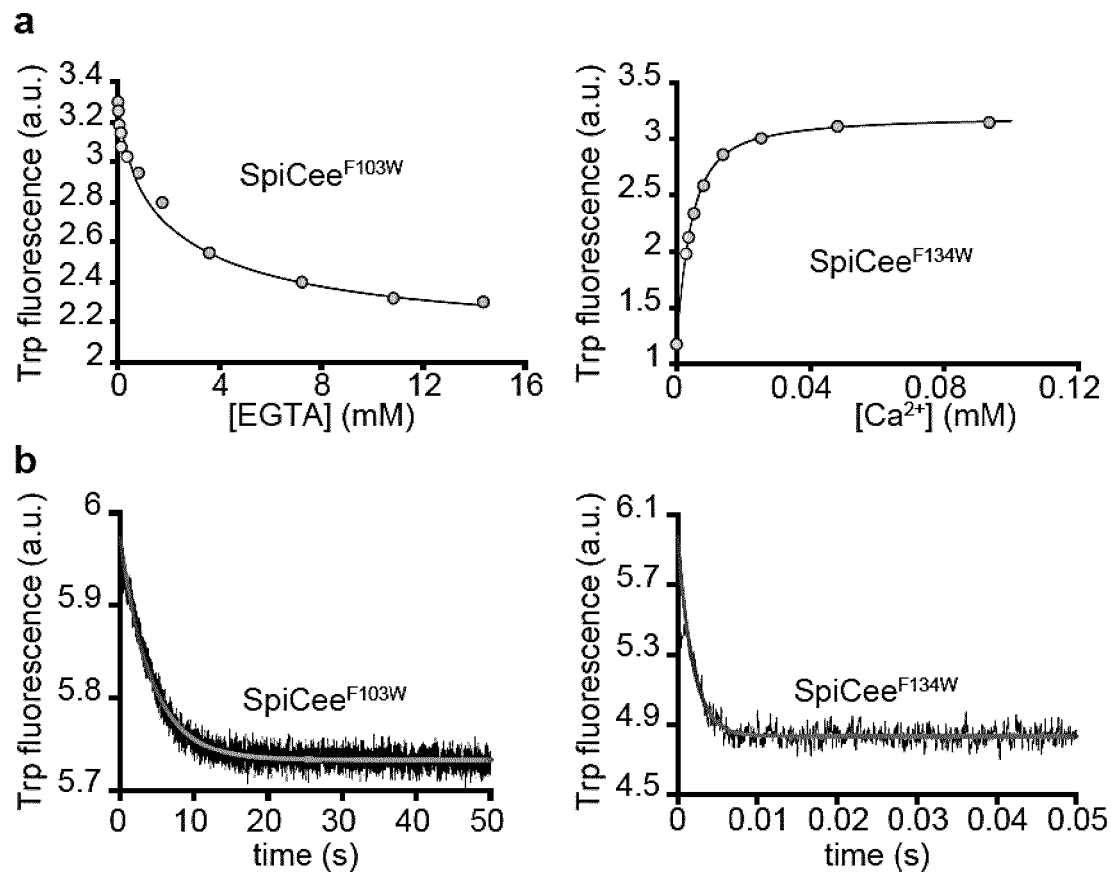
FIG. 5. Biochemical characterization of $^{Ca2+}$Sp/SpiCee. (a) $^{Ca2+}$Sp/SpiCee$^{F103W}$ enabled to determine the dissociation constant of $Ca^{2+}$ from the EF hand adjacent to the inserted tryptophan (residue 103) by competition with EGTA (Kd=0.3±0.1 nM), whereas direct $Ca^{2+}$ titration was used with $^{Ca2+}$Sp/SpiCee$^{F134W}$ to measure the Kd of the calmodulin-derived $Ca^{2+}$-binding site in the vicinity of the mutation (Kd=2.8±0.9 μM). Representative titration fits are shown. (b) Stopped-flow experiments were conducted to determine the kinetic dissociation constants of $^{Ca2+}$Sp/SpiCee$^{F103W}$ and $^{Ca2+}$Sp/SpiCee$^{F134W}$ ($k_{off}$=529±28 s$^{-1}$ and $k_{off}$=0.24±0.01 s$^{-1}$ respectively).
Figure 6:
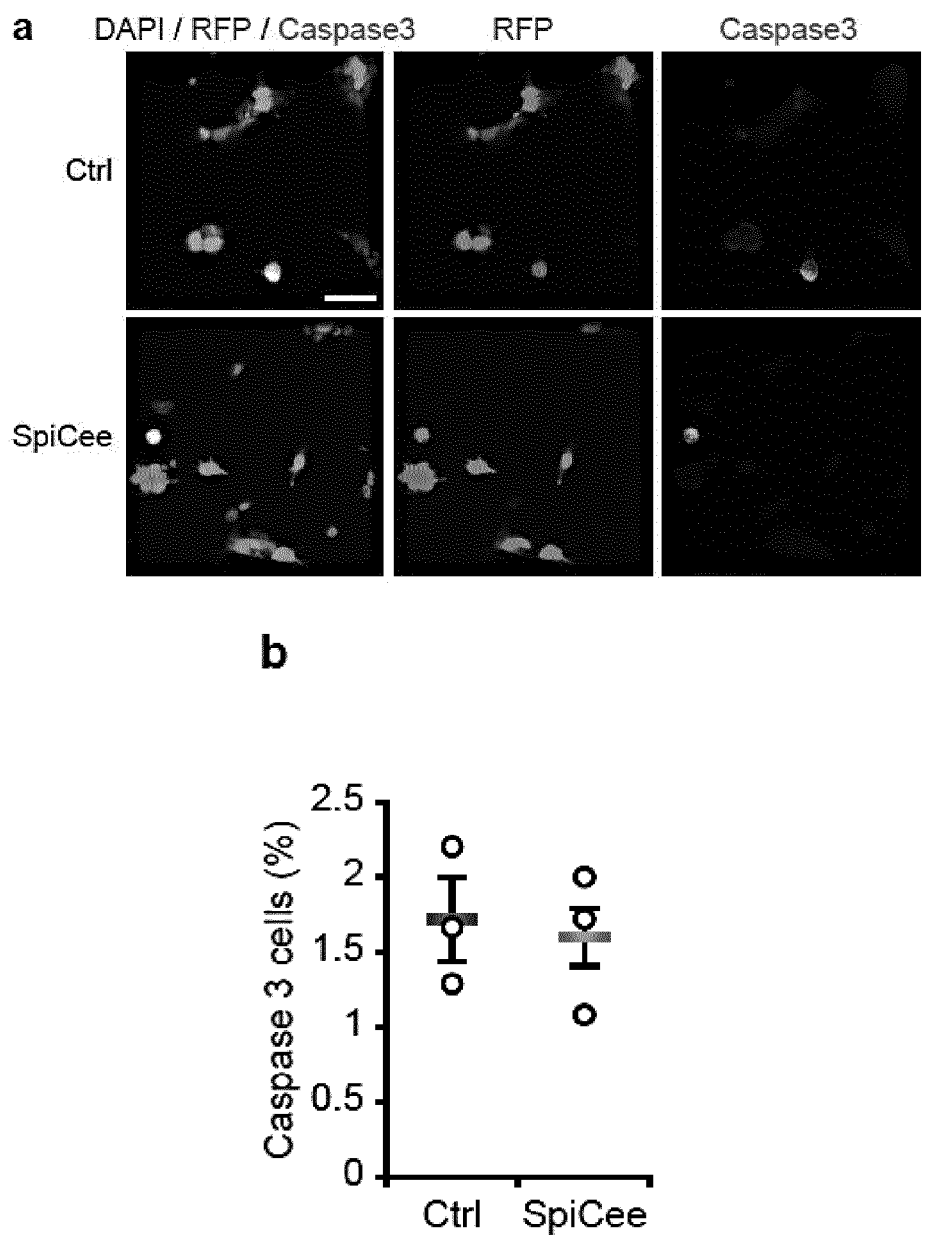
FIG. 6. $^{Ca2+}$Sp/SpiCee does not affect cell survival. HEK293 cells were transfected with either $^{Ca2+}$Sp/SpiCee or RFP. Activated Caspase 3 positive cells were immunolabeled to evaluate the number of cells undergoing apoptosis. $^{Ca2+}$Sp/SpiCee-expressing cells are not more prone to enter an apoptotic program than their RFP-expressing controls. (a) Scale bar, 50 μm (b) Data are mean±s.e.m., Mann-Whitney test.
Figure 7:
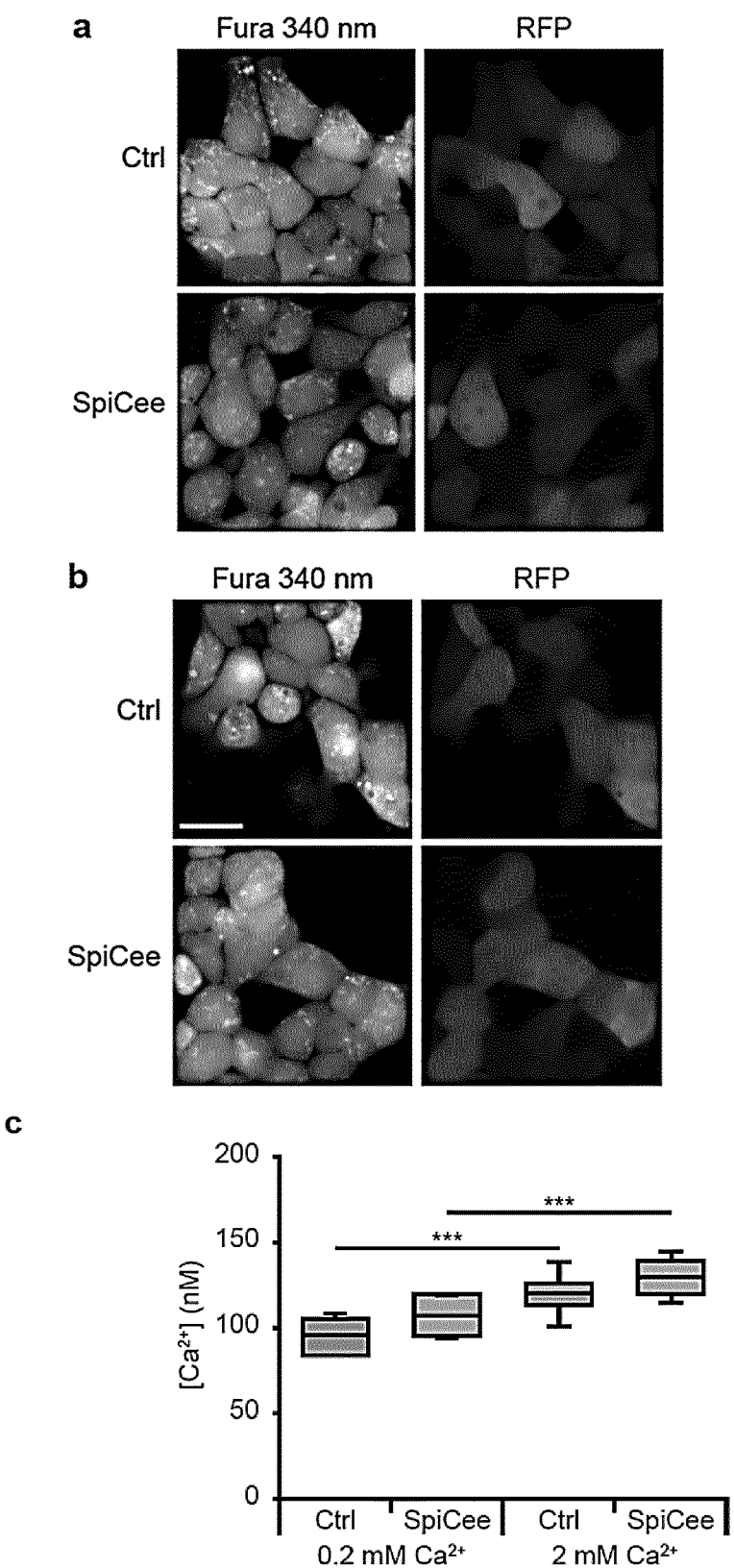
FIG. 7. $^{Ca2+}$Sp/SpiCee-transfected cells adapt to maintain a resting concentration of $Ca^{2+}$ similar to their controls. $^{Ca2+}$Sp/SpiCee- or RFP-transfected HEK293 cells were loaded with the ratiometric calcium sensor Fura-2, enabling to evaluate their intracellular calcium concentration. (a) Fura-2 was sequentially excited at 340 nm ($Ca^{2+}$ bound) and 380 nm ($Ca^{2+}$ free), and the intracellular $Ca^{2+}$ concentration was computed based on the fluorescence of calibrated $Ca^{2+}$ solutions. No difference in the resting $Ca^{2+}$ concentration was detected between $^{Ca2+}$Sp/SpiCee- and RFP-transfected cell in culture media containing either (a) 0.2 mM or (b) 2 mM $Ca^{2+}$. (c) The $Ca^{2+}$ resting concentration is higher in both $^{Ca2+}$Sp/SpiCee- and RFP-transfected cells grown in 2 mM extracellular $Ca^{2+}$ as compared to cells kept in 0.2 mM $Ca^{2+}$, suggesting that $^{Ca2+}$Sp/SpiCee does not prevent the regulation of the intracellular resting concentration of this ion. (a, b) Scale bar, 20 μm. scale bar in (b) applies to (a). (c) Box-and-whisker plot elements: center line, mean; box limits, upper and lower quartiles; whiskers, s.d.; ***P ⊩ 0.001, Kruskal-Wallis test followed by Dunn's multiple comparison test.

To characterize the Ca$^{2+}$ binding properties of $^{Ca2+}$Sp/SpiCee, we used the tryptophan fluorescence of two variants of $^{Ca2+}$Sp/SpiCee ($^{Ca2+}$Sp/SpiCee$^{F134W}$ and $^{Ca2+}$Sp/SpiCee$^{F103W}$). Each of these mutants enables the evaluation of the Ca$^{2+}$ binding properties of either the calmodulin or the parvalbumin moiety ($^{Ca2+}$Sp/SpiCee$^{F134W}$ and $^{Ca2+}$Sp/SpiCee$^{F103W}$ respectively). Using Ca$^{2+}$ titration, we found that $^{Ca2+}$Sp/SpiCee$^{F134W}$ has a Kd for Ca$^{2+}$ of 2.8±0.9 µM and stopped-flow experiments were performed to evaluate its dissociation rate, koff=529±28 s$^{-1}$ at 20° C. (FIG. 5). The high affinity of the labeled parvalbumin site ($^{Ca2+}$Sp/SpiCee$^{F103W}$) prevented the use of Ca$^{2+}$ titration and the Kd was measured by competition with EGTA. The dissociation constant of $^{Ca2+}$Sp/SpiCee$^{F103W}$ is Kd=0.3±0.1 nM and a koff=0.24±0.01 s$^{-1}$ (FIG. 5). These features match the Ca$^{2+}$ binding properties of the full length parvalbumin and calmodulin proteins and confirm that $^{Ca2+}$Sp/SpiCee is a bimodal Ca$^{2+}$ chelator combining sites with low and high affinity for Ca$^{2+}$. $^{Ca2+}$Sp/SpiCee was expressed in HEK293 cells to evaluate its behavior in cellulo. Expressing $^{Ca2+}$Sp/SpCee did not affect cell survival (FIG. 6) nor the resting Ca$^{2+}$ concentration (FIG. 7), suggesting that $^{Ca2+}$Sp/SpiCee-expressing cells can maintain a resting Ca$^{2+}$ concentration compatible with their survival, within the previously reported range. $^{Ca2+}$Sp/SpiCee-transfected cells were also able to adapt their resting Ca$^{2+}$ concentration to the amount of Ca$^{2+}$ in the culture medium (FIG. 7). These observations are similar to the reported properties of pharmacological Ca$^{2+}$ buffers.

Figure 8:
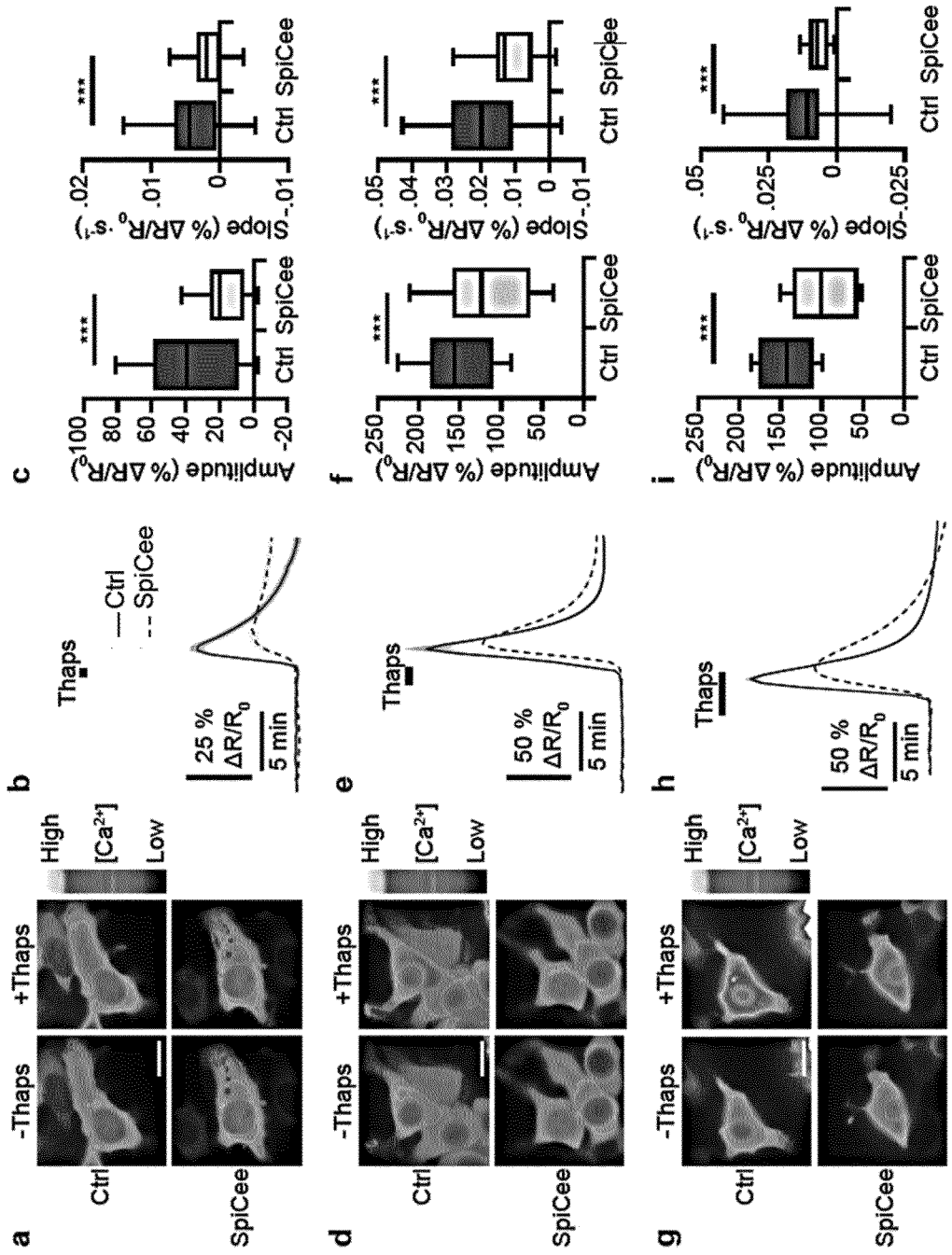
FIG. 8. $^{Ca2+}$Sp/SpiCee reduces the elevation of Ca$^{2+}$ concentration induced by brief or longer pulses of thapsigargin. HEK293 cells were bathed with a low Ca$^{2+}$ medium and challenged with a 1 min (a-c), 2 min (d-f) and 5 min (g-i) pulse of thapsigargin. $^{Ca2+}$Sp/SpiCee-expressing cells display a reduced FRET/CFP ratio elevation compared to controls, and a delayed maximum response. The decay of the response is also delayed in SpiCee-expressing cells, reducing the sharpness of the response. Scale bars, 20 µm. (b, e, h) Data are mean±s.e.m. (c, f, i) Box-and-whisker plot elements: center line, mean; box limits, upper and lower quartiles; whiskers, s.d.; ***P ⊬ 0.001, Mann-Whitney test.
Figure 9:
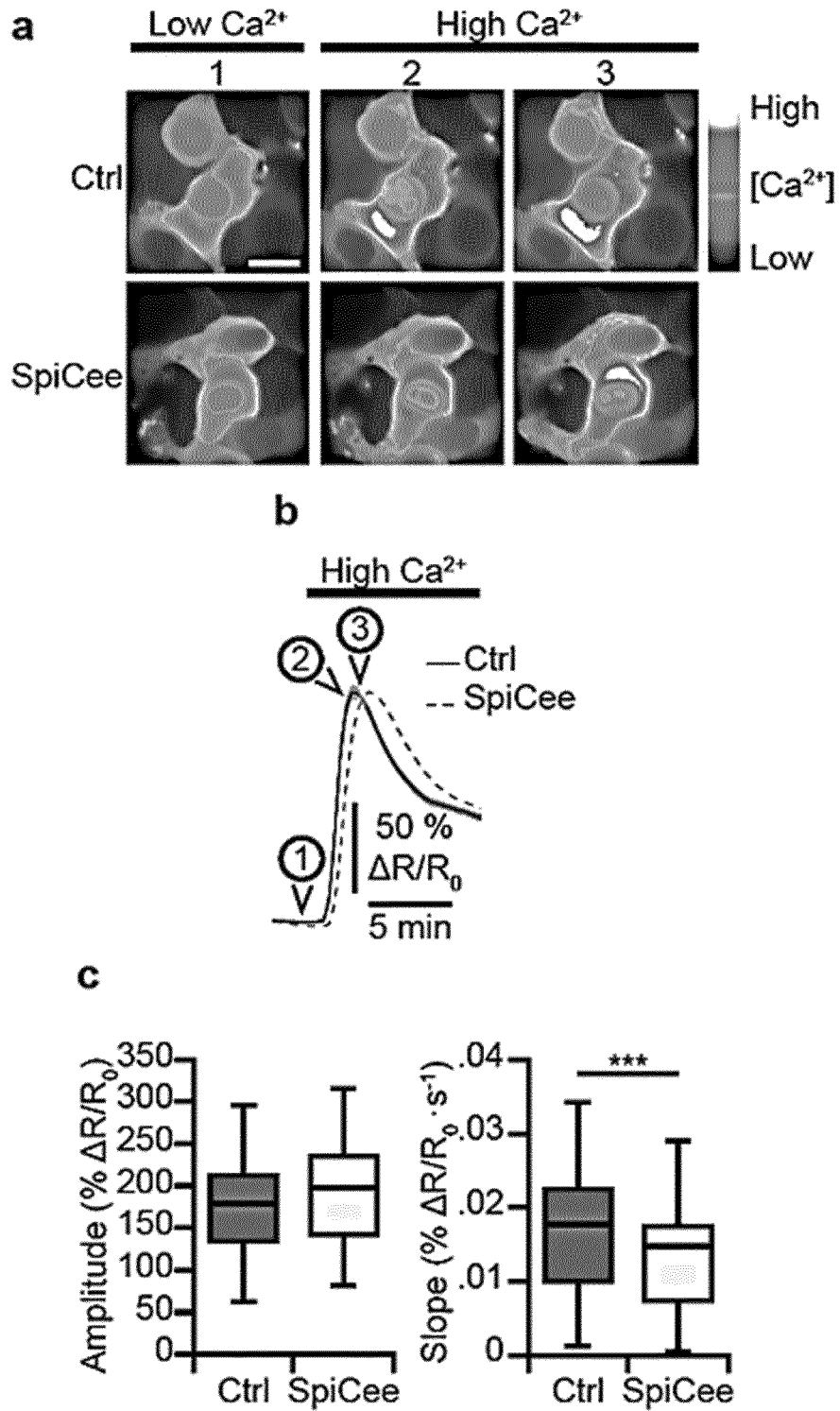
FIG. 9. Massive and sustained elevation of intracellular Ca$^{2+}$ concentration is delayed by $^{Ca2+}$Sp/SpiCee. A change of extracellular Ca$^{2+}$ concentration (from 0.2 mM to 2 mM) generates a massive change in the Twitch2B FRET/CFP ratio in HEK293 cells. Cells expressing $^{Ca2+}$Sp/SpiCee exhibit a change in the FRET/CFP ratio of similar magnitude, but delayed as compared to cells devoid of $^{Ca2+}$Sp/SpiCee. Scale bar, 20 µm. (b) Data are mean±s.e.m. (c) Box-and-whisker plot elements: center line, mean; box limits, upper and lower quartiles; whiskers, s.d.; ***P ⊬ 0.001, Mann-Whitney test.

The buffering properties of $^{Ca2+}$Sp/SpiCee were investigated using Twitch2B, an optimized Ca$^{2+}$ FRET sensor. The FRET over CFP ratio, reflecting intracellular Ca$^{2+}$ concentration, was monitored in Twitch2B-expressing HEK293 cells. The release of intracellular Ca$^{2+}$ stores induced by a 20 s pulse of thapsigargin induced an increase in FRET/CFP ratio, that was drastically reduced in cells co-expressing $^{Ca2+}$Sp/SpiCee (FIG. 1). The lack of FRET/CFP ratio elevation in presence of thapsigargin reveals that $^{Ca2+}$Sp/SpiCee compete with other Ca$^{2+}$-binding proteins, including Twitch2B, preventing them to bind efficiently to Ca$^{2+}$. To investigate the limits of Ca$^{2+}$ buffering by $^{Ca2+}$Sp/SpiCee, cells co-expressing $^{Ca2+}$Sp/SpiCee and Twitch2B were exposed to longer thapsigargin stimulation (1, 2 or 5 min). In all cases, $^{Ca2+}$Sp/SpiCee reduced and delayed the Ca$^{2+}$ elevation detected by the biosensor (FIG. 8). Extreme intracellular Ca$^{2+}$ elevations were induced by increasing the extracellular Ca$^{2+}$ level (from 0.2 mM to 2 mM), after prolonged thapsigargin exposure. $^{Ca2+}$Sp/SpiCee induced a delay in the Ca$^{2+}$ elevation detected by Twitch2B (FIG. 9). This demonstrate that $^{Ca2+}$Sp/SpiCee is able to alter pharmacologically-induced Ca$^{2+}$ signaling in a wide range of concentration of this second messenger.

Figure 4:
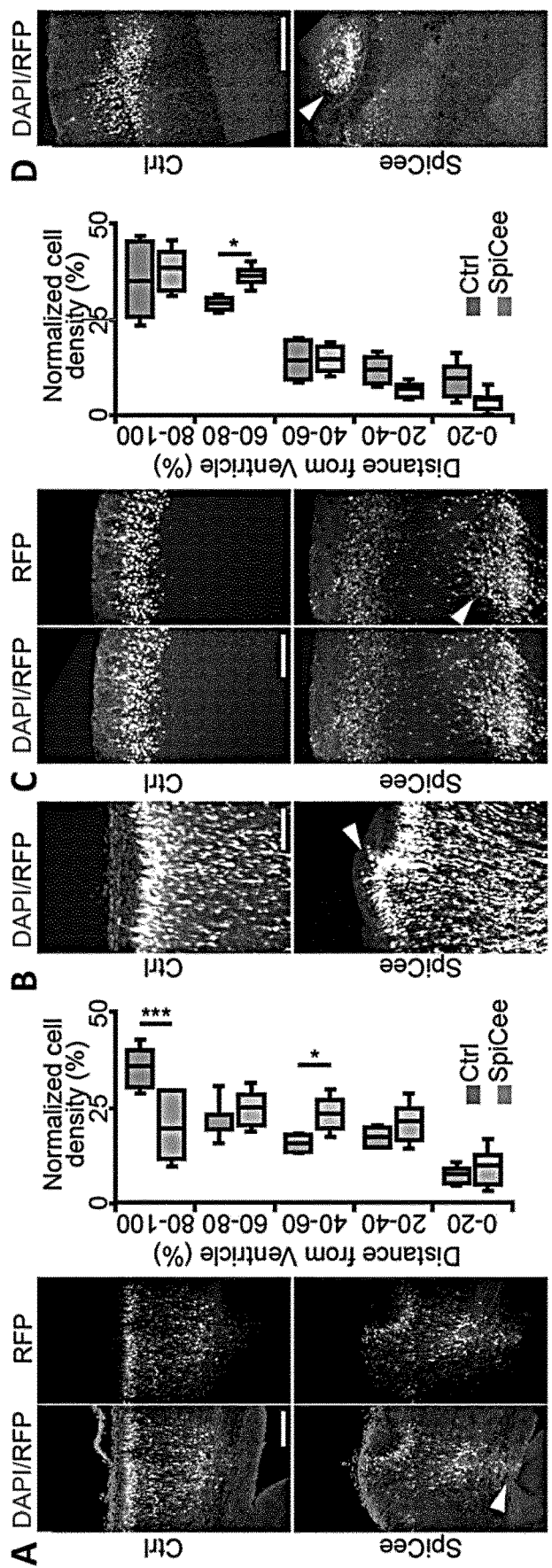
FIG. 4. (A,B) Control cortical neurons electroporated at E14.5 form a dense layer close to the marginal zone at E18.5. $^{Ca2+}$Sp/SpiCee-expression prevents the development of this layer, with (A) neurons scattered throughout the depth of the developing cortex (arrowhead), and (B) the formation of heterotopia at the surface of the cortex (arrowhead). (C) In P10 pups, $^{Ca2+}$Sp/SpiCee-electroporated neurons have a wider spread in the cortex than controls and (D) heterotopias induced by $^{Ca2+}$Sp/SpiCee are maintained (arrowhead), indicating that altering $Ca^{2+}$ signaling interferes with cortical neuron migration. Box-and-whisker plot elements: center line, mean; box limits, upper and lower quartiles; whiskers, s.d. Scale bars, (A) 250 μm, (B) 100 μm, (C) 200 μm, (D) 500 μm. *P ⊩ 0.05; ***P ⊩ 0.001; (A,C) Two-way ANOVA and Bonferroni post hoc tests.

To assess $^{Ca2+}$Sp/SpiCee capability to interfere with physiological processes in vivo, $^{Ca2+}$Sp/SpiCee was expressed in newly generated cortical neurons using in utero electroporation of the lateral ventricle in 14.5 day-old (E14.5) mice embryos. The migration of early born cortical neurons is a Ca$^{2+-}$dependent process. The position of migrating electroporated neurons was assessed at E18.5. The majority of GFP and mRFP co-electroporated neurons reached the cortical plate, and form a dense layer of neuron near the marginal zone (FIG. 4). In contrast, many neurons co-expressing GFP and $^{Ca2+}$Sp/SpiCee exhibited reduced migration and were found throughout the neocortex, including the subventricular zone. In addition, several electroporated cells failed to stall at the cortical plate, overshooting towards the marginal zone and causing heterotopias. (FIG. 1). Several electroporated neurons also failed to stall at the cortical plate, overshooting toward the marginal zone and causing heterotopias in 7 out of 9 animals, misplaced neurons were found in only 2 out of 10 mRFP-electroporated embryos (FIG. 4). At postnatal day 10, $^{Ca2+}$Sp/SpiCee-expressing neurons covered a thicker layer of the cortex than their mRFP-electroporated controls (FIG. 4). Furthermore, the heterotopias detected during embryonic development were maintained at post-natal stages in $^{Ca2+}$Sp/SpiCee-expressing animals (10 out of 12), whereas they were just found in 1 mRFP electroporated pup (5 electroporated animals, FIG. 4). This demonstrates that Ca$^{2+}$ buffering by $^{Ca2+}$Sp/SpiCee is sufficient to alter the physiological Ca$^{2+}$ modulation required for correct neuronal migration in vivo.

Figure 2:
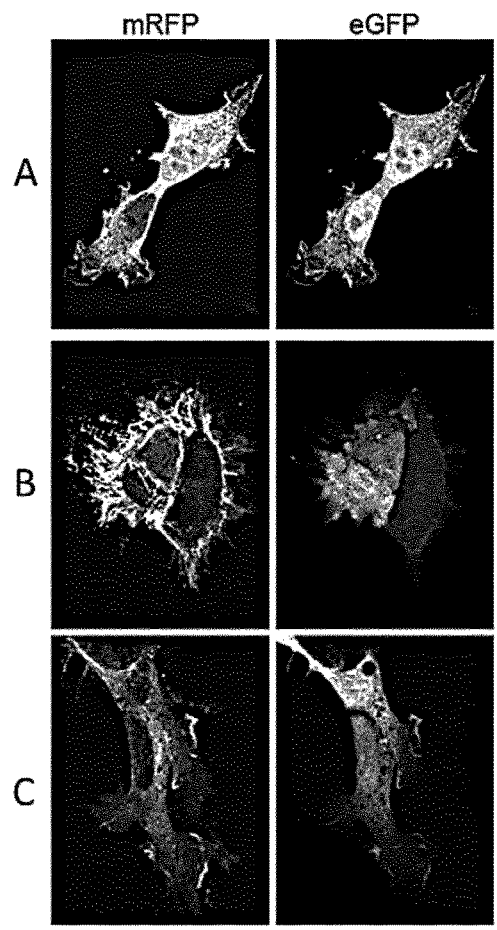
FIG. 2. Subcellular restriction of $Ca^{2+}$ manipulation using the polypeptide of the invention. A: $^{Ca2+}$Sp/SpiCee, B: Lyn-$^{Ca2+}$Sp/SpiCee, C: $^{Ca2+}$Sp/SpiCee-Kras. $^{Ca2+}$Sp/SpiCee was either used to globally alter $Ca^{2+}$ signaling when not targeted to any cellular compartment or to target specific compartments. Lyn-$^{Ca2+}$Sp/SpiCee aims to target to lipid rafts whether $^{Ca2+}$Sp/SpiCee-Kras is intended to be restricted to the non-raft fraction of the plasma membrane. $^{Ca2+}$Sp/SpiCee was detected in the cytoplasm whether both Lyn-$^{Ca2+}$Sp/SpiCee and $^{Ca2+}$Sp/SpiCee-Kras were found at the plasma membrane.
Figure 3:
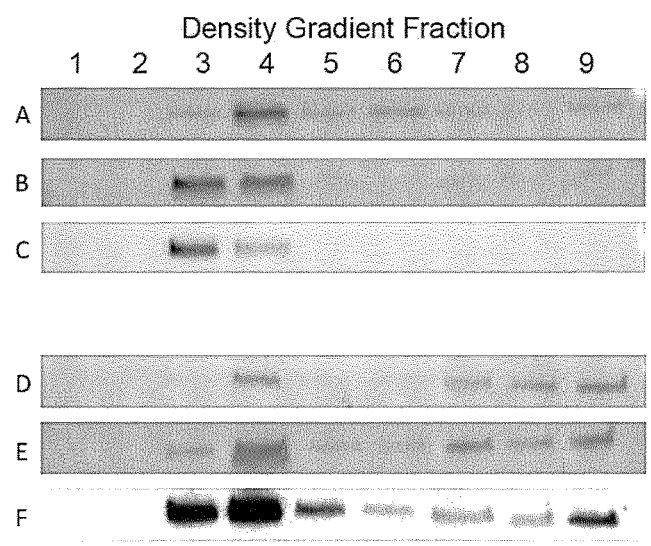
FIG. 3. Plasma membrane fractionation highlighted distinct subcellular localization of Lyn-$^{Ca2+}$Sp/SpiCee and $^{Ca2+}$Sp/SpiCee-Kras. Presence of proteins of interest in different density gradient fraction. A: Caveolin, B: Lyn-Twitch2B, C: Lyn-$^{Ca2+}$Sp/SpiCee, D: Adaptin, E: Twitch2B-Kras, F: $^{Ca2+}$Sp/SpiCee-Kras. Lyn-$^{Ca2+}$Sp/SpiCee was highly enriched in fraction 3 whether the localization of $^{Ca2+}$Sp/SpiCee-Kras was shifted towards higher density fractions (4 to 9).
Figure 10:
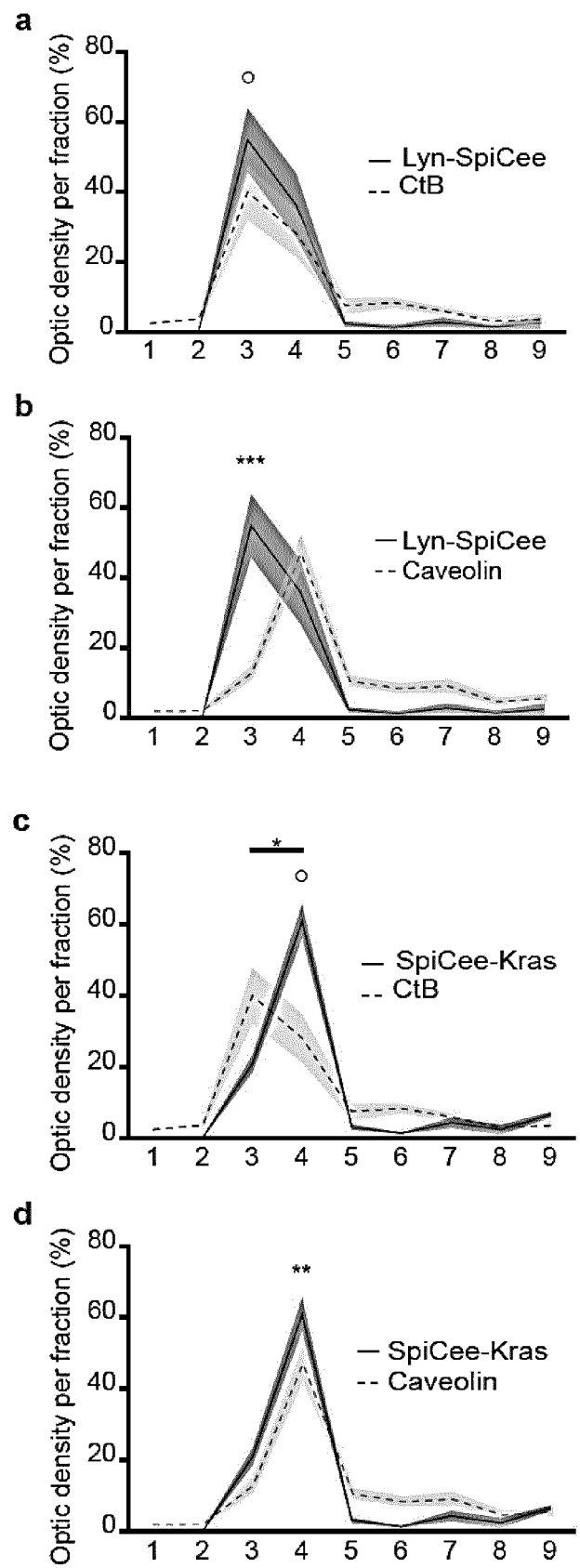
FIG. 10. Biochemical characterization of the $^{Ca2+}$Sp/SpiCee targeting. (a, b) Lyn-$^{Ca2+}$Sp/SpiCee peaks in fractions 3 in a membrane fractionation assay. (a) It coincides with the expression profile of the β subunit of cholera toxin (CtB, enriched in fractions 3 and 4, peaks in fraction 3) and (b) differs from the expression of Caveolin (enriched 2+$_{sp}$ in fraction 4). $^{Ca2+}$Sp/SpiCee-Kras is mostly enriched in fraction 4, with a profile resembling (d) Caveolin, and (c) distinct from CtB. Data are mean±s.e.m.; *P ⊬ 0.05, *P ⊬ 0.01, *P ⊬ 0.001, Two-way ANOVA and Bonferroni post hoc tests.

Calcium signals in the cell are often restricted to subcellular compartments. Since genetic-encoding confers the ability to restrict the expression of the constructs to a specific organelle, the functionality of $^{Ca2+}$Sp/SpiCee in this scenario was assessed. A tandem of palmitoylation-myristoylation motifs from Lyn Kinase was fused to the n-terminus of $^{Ca2+}$Sp/SpiCee to target lipid rafts, a compartment of the plasma membrane (Lyn-$^{Ca2+}$Sp/SpiCee). Alternatively $^{Ca2+}$Sp/SpiCee was excluded from lipid rafts but still targeted to the plasma membrane by the c-terminus fusion of the CaaX-polylysine motif derived from K-Ras ($^{Ca2+}$Sp/SpiCee-Kras). These targeting sequences have been previously used and validated. Using detergent-free plasma membrane fractionation methods, Lyn-$^{Ca2+}$Sp/SpiCee was found enriched in lipid raft fractions, whereas $^{Ca2+}$Sp/SpiCee localization was shifted towards the non-raft fractions (FIG. 2), demonstrating that these variants of $^{Ca2+}$Sp/SpiCee are targeted to distinct membrane compartments. Their specific distribution matches the profile of different membrane markers, the H subunit of cholera toxin (CtB) and caveolin respectively (FIG. 10).

Figure 11:
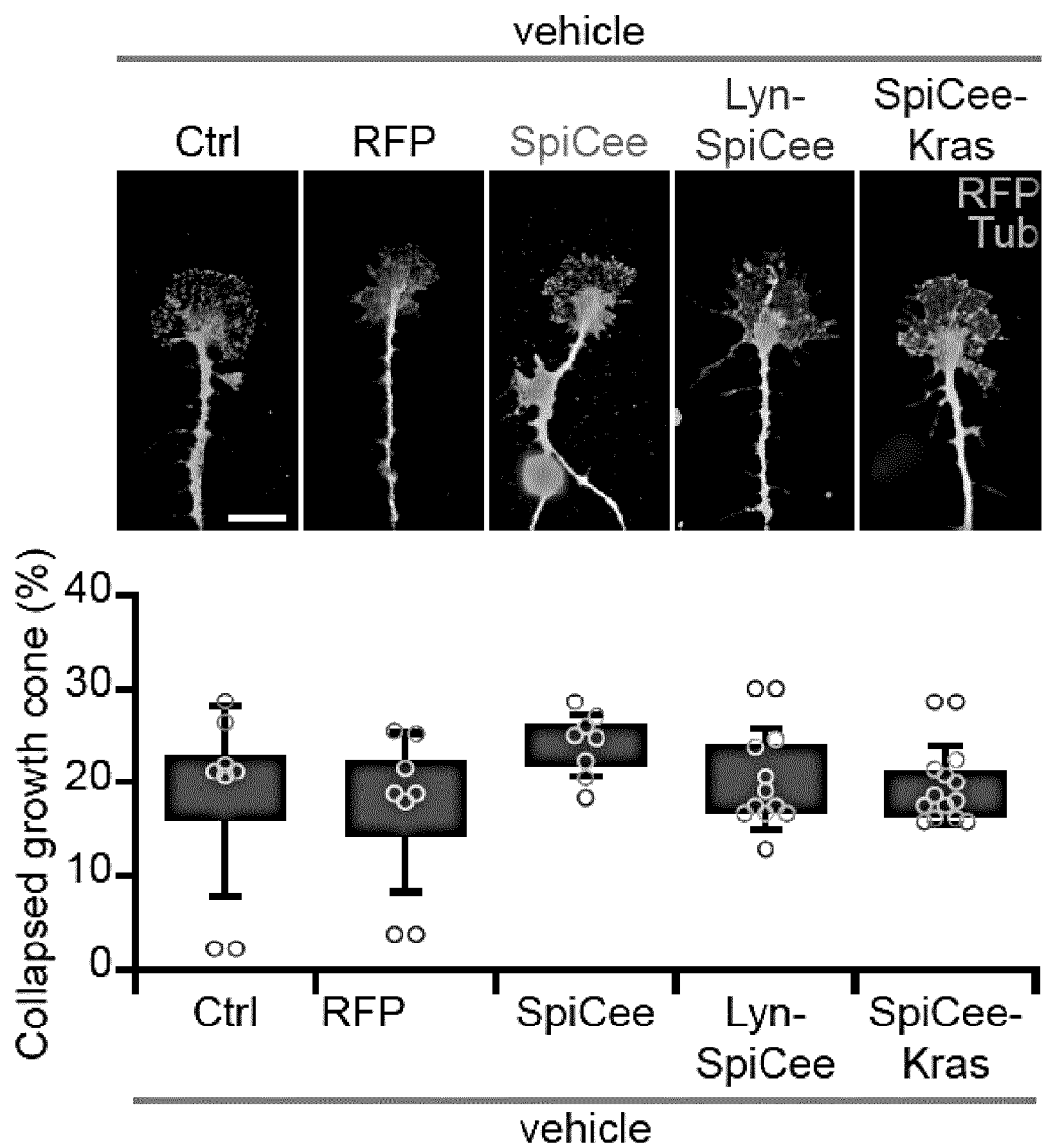
FIG. 11. $^{Ca2+}$Sp/SpiCee, Lyn-$^{Ca2+}$Sp/SpiCee and $^{Ca2+}$Sp/SpiCee-Kras do not affect the morphology of growing axons. Non-electroporated RGC axons display a fan-shaped growth cone at their tip which is not affected by the expression of mRFP, $^{Ca2+}$Sp/SpiCee, Lyn-$^{Ca2+}$Sp/SpiCee or $^{Ca2+}$Sp/SpiCee-Kras. Box-and-whisker plot elements: center line, mean; box limits, upper and lower quartiles; whiskers, s.d. Scale bar, 10 µm. No significant differences are detected; Kruskall-Wallis test.
Figure 12:
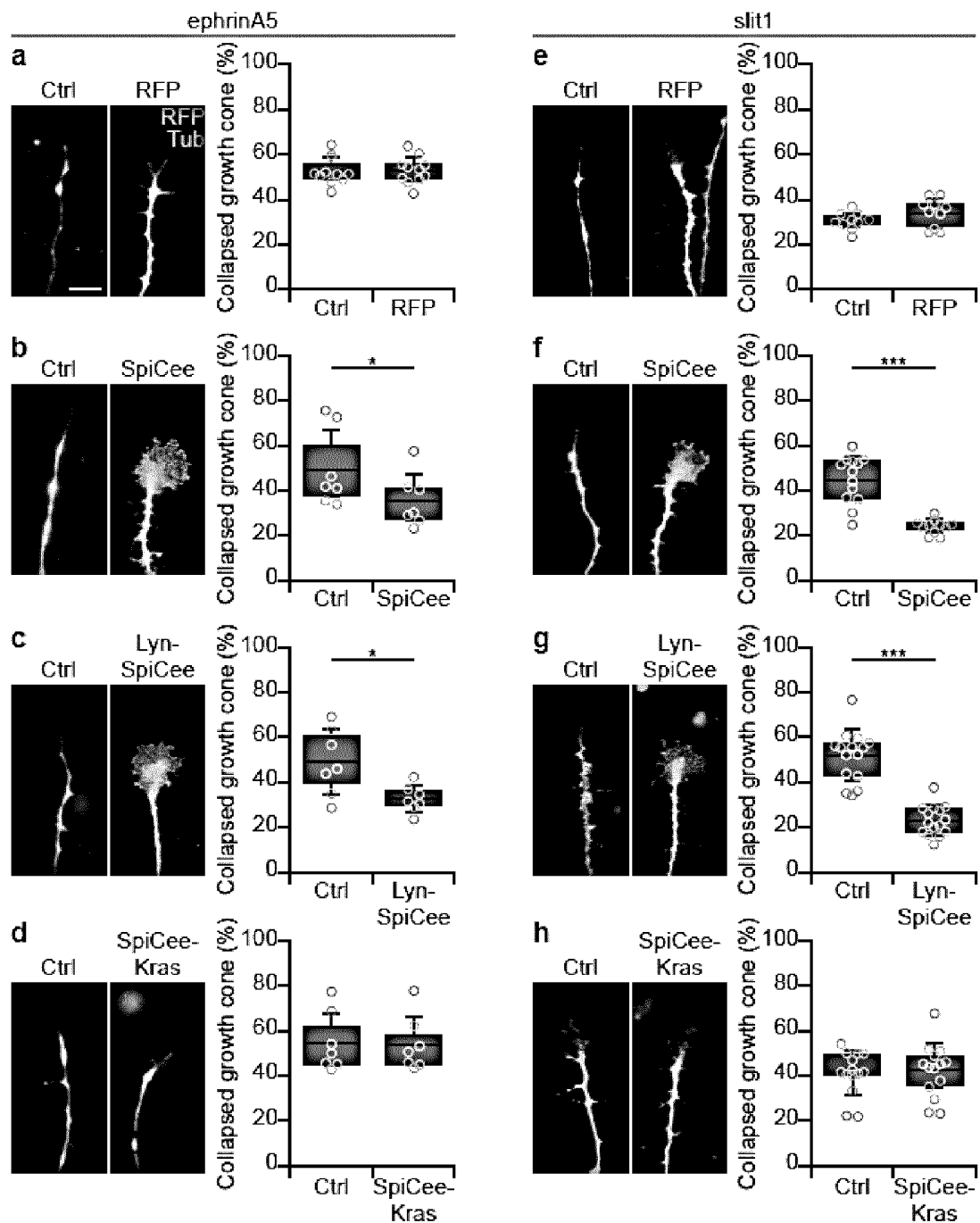
FIG. 12. Cytosolic $^{Ca2+}$Sp/SpiCee and Lyn-$^{Ca2+}$Sp/SpiCee but not $^{Ca2+}$Sp/SpiCee-Kras prevent ephrinA5- and Slit1-induced growth cone collapse. When exposed to (a) ephrinA5 or (e) slit1, mRFP-expressing growth cones exhibit the same collapse response than their non-electroporated neighbors of the same coverslips, (b, f) $^{Ca2+}$Sp/SpiCee- and (c, g) Lyn-$^{Ca2+}$Sp/SpiCee-expressing axons are resistant to the repellent activity of ephrinA5 and slit1, that is observed in the non-electroporated axons from the same coverslip. (d, h) In contrast, $^{Ca2+}$Sp/SpiCee-Kras-expressing axons exhibit similar growth cone remodeling to their controls. Box-and-whisker plot elements: center line, mean; box limits, upper and lower quartiles; whiskers, s.d. Scale bar, 10 µm. *P ⊬ 0.05; ***P ⊬ 0.001; Wilcoxon paired test

Using Lyn-$^{Ca2+}$Sp/SpiCee and $^{Ca2+}$Sp/SpiCee-Kras, the potential of $^{Ca2+}$Sp/SpiCee to manipulate specific physiological Ca$^{2+}$ dependent cellular processes depending on its subcellular localization was investigated. To this aim the response of retinal axons to the repellent guidance molecules slit1 and ephrinA5 was analyzed, a process requiring calcium signaling. In control conditions, including untransfected axons and mRFP-electroporated axons, slit1 and ephrinA5 induced the collapse of non-electroporated or mRFP-expressing growth cones, characterized by the depolymerization of lamellipodial actin and drastic reduction of the growth cone area (FIGS. 11 and 12). The expression of $^{Ca2+}$Sp/SpiCee in the cytosol completely abolished slit1- and ephrinA5-induced growth cone collapse, confirming the requirement of calcium signaling (FIG. 12). Similarly, Lyn-$^{Ca2+}$Sp/SpiCee-expressing axons showed no increase in collapse upon Slit-1 treatment (FIG. 12). In contrast, $^{Ca2+}$Sp/SpiCee-Kras-expressing axons were indistinguishable from controls (FIG. 12), demonstrating that the collapse-inducing signaling cascades generated by slit1 and ephrinA5 require compartmentalized calcium signaling in lipid rafts, and that targeted versions of $^{Ca2+}$Sp/SpiCee achieve specific manipulation of distinct subcellular and $Ca^{2+}$ dependent signaling cascades.

In conclusion, the polypeptide of the invention functions as a $Ca^{2+}$ scavenger that has the capability to interfere with $Ca^{2+}$-dependent physiological functions. The polypeptide of the invention has the potential to alter calcium responses in a cell-specific manner and with subcellular resolution, opening new fields for the precise study of signaling cascades and paving the way for therapeutic implementation.

The invention claimed is:

1. A polypeptide comprising a first calcium-binding domain, a peptide linker and a second calcium binding domain, wherein said first and second binding domains are linked through said peptide linker, and wherein:
the first calcium-binding domain and the second calcium binding domain each comprises at least one calcium-binding site derived from a EF-hand motif; and
the first calcium-binding domain and the second calcium binding domain differ in at least one calcium-binding site, wherein:
the first calcium-binding domain comprises at least one calcium-binding site comprising a calcium-binding loop from Parvalbumin chosen in the list consisting of SEQ ID NO: 2 to 5 and
the second calcium-binding domain comprises at least one calcium-binding site comprising a calcium-binding loop from Calmodulin chosen in the list consisting of SEQ ID NO: 6 to 9.

2. The polypeptide according to claim 1, wherein the polypeptide further comprises a peptide signal.

3. The polypeptide according to claim 1, wherein the polypeptide further comprises a fluorescent peptide.

4. A pharmaceutical composition comprising at least one polypeptide according to claim 1 and a pharmaceutically acceptable carrier.

5. A method of stabilizing calcium concentration and/or of inhibiting calcium signalization in vivo or in vitro, comprising contacting calcium with an effective amount of the polypeptide of claim 1.

6. A method of treating a disorder in a subject treatable by chelating calcium, comprising administering to the subject an effective amount of the polypeptide of claim 1 or a pharmaceutical composition comprising the polypeptide of claim 1 and a pharmaceutically acceptable carrier.

7. A method of treating a pathology associated with intracellular calcium signaling dysfunction, comprising administering to a subject in need thereof a therapeutic amount of the polypeptide as recited in claim 1 or a pharmaceutical composition comprising the polypeptide of claim 1 and a pharmaceutically acceptable carrier.

8. The method of claim 7, wherein the pathology associated with intracellular calcium signaling dysfunction is retinitis pigmentosa, a neurodegenerative disease, Alzheimer disease, epilepsy, stroke, cardiac dysrhythmia, heart failure, hypertension, diabetes, or cancer.

9. The polypeptide according to claim 2, wherein the peptide signal targets the polypeptide to the plasma membrane.

10. The polypeptide of claim 9, wherein the peptide signal comprises SEQ ID NO: 20 or 21 or a functional variant thereof.

11. The polypeptide according to claim 3, wherein the fluorescent peptide is selected from the group consisting of green fluorescent protein (GFP), cyan fluorescent protein (CFP), yellow fluorescent protein (YFP) and red fluorescent protein (RFP).

12. The polypeptide according to claim 1, wherein the first calcium-binding domain comprises at least one calcium-binding site consisting of calcium-binding loop from Parvalbumin chosen in the list consisting of SEQ ID NO: 2 to 5.

13. The polypeptide according to claim 1, wherein the second calcium-binding domain comprises at least one calcium-binding site consisting of calcium-binding loop from Calmodulin chosen in the list consisting of SEQ ID NO: 6 to 9.

14. The polypeptide according to claim 1, wherein:
the first calcium-binding domain comprising at least two calcium-binding sites comprising calcium-binding loop from Parvalbumin chosen in the list consisting of SEQ ID NO: 2 to 5 and
the second calcium-binding domain comprising at least two calcium-binding sites comprising calcium-binding loop from Calmodulin chosen in the list consisting of SEQ ID NO: 6 to 9.

15. The polypeptide according to claim 1, wherein:
the calcium-binding loop from Parvalbumin is chosen in the list consisting of SEQ ID NO: 4 or SEQ ID NO: 5 and
the calcium-binding loop from Calmodulin is chosen in the list consisting of SEQ ID NO: 6 or SEQ ID NO: 7.

16. The polypeptide according to claim 1, wherein the first calcium-binding domain comprises of at least one calcium-binding site comprising EF-hand motifs from Parvalbumin chosen in the list consisting of SEQ ID NO: 10 to SEQ ID NO: 11, and a functional variant thereof having a sequence which has at least 95% identity with the sequence SEQ ID NO: 10 or SEQ ID NO: 11 and which is a peptide which sequence derives from SEQ ID NO: 10 or SEQ ID NO: 11 by conservative substitutions.

17. The polypeptide according to claim 1, wherein the second calcium-binding domain comprises at least one calcium-binding site comprising EF-hand motifs from Calmodulin chosen in the list consisting of SEQ ID NO: 12 to 15 and a functional variant thereof having a sequence which has at least 95% identity with the sequence chosen in the list consisting of SEQ ID NO: 12 to 15 and which is a peptide which sequence derives from the sequence chosen in the list consisting of SEQ ID NO: 12 to 15 by conservative substitutions.

18. The polypeptide according to claim 1, wherein:
the first calcium-binding domain has a sequence comprising the sequence SEQ ID NO: 16 or a functional variant thereof having a sequence which has at least 95% identity with the sequence SEQ ID NO: 16 and which is a peptide which sequence derives from sequence SEQ ID NO: 16 by conservative substitutions and
the second calcium-binding domain has a sequence comprising the sequence SEQ ID NO: 17 or functional variant thereof having a sequence which has at least 95% identity with the sequence SEQ ID NO: 17 and which is a peptide which sequence derives from sequence SEQ ID NO: 17 by conservative substitutions.

19. The polypeptide according to claim 1, wherein the polypeptide has the sequence SEQ ID NO: 19.

* * * * *